(12) United States Patent
Wagner et al.

(10) Patent No.: US 8,003,362 B2
(45) Date of Patent: Aug. 23, 2011

(54) METHODS AND CONSTRUCTS FOR HIGH YIELD EXPRESSION OF CLOSTRIPAIN

(75) Inventors: Fred W. Wagner, Walton, NE (US); Peng Luan, Fishers, IN (US); Yuannan Xia, Lincoln, NE (US); Barton Holmquist, Eagle, NE (US)

(73) Assignee: Medtronic Inc., Minneapolis, MN (US)

( * ) Notice: Subject to any disclaimer, the term of this patent is extended or adjusted under 35 U.S.C. 154(b) by 497 days.

(21) Appl. No.: 10/997,697

(22) Filed: Nov. 24, 2004

(65) Prior Publication Data

US 2005/0244924 A1    Nov. 3, 2005

Related U.S. Application Data

(63) Continuation of application No. PCT/US03/16642, filed on May 23, 2003.

(60) Provisional application No. 60/383,357, filed on May 24, 2002.

(51) Int. Cl.
*C12N 9/48* (2006.01)
*C12N 1/20* (2006.01)
*C12N 15/74* (2006.01)
*C07K 1/00* (2006.01)

(52) U.S. Cl. .................. 435/212; 435/252.33; 435/488; 530/350

(58) Field of Classification Search .................. None
See application file for complete search history.

(56) References Cited

U.S. PATENT DOCUMENTS

| 5,602,034 A | 2/1997 | Tekamp-Olson |
| 5,719,021 A * | 2/1998 | Inouye ............................ 435/6 |
| 5,853,976 A | 12/1998 | Hesse et al. |
| 7,186,539 B1 * | 3/2007 | Tomaselli et al. ........... 435/219 |

FOREIGN PATENT DOCUMENTS

| EP | 473128 A * | 3/1992 |
| WO | WO-0026418 A1 | 5/2000 |

OTHER PUBLICATIONS

Herrero et al., 1990, Journal of Bacteriology, vol. 172(11), pp. 6557-6567.*
Wanker et al.,1991, J. of Biotechnol., vol. 18(3), pp. 243-254.*
Piper et al., 1988, Nucleic Acid, vol. 16, pp. 1333-1348.*
Marczinovits et al., An alternative purification protocol for producing hepatitis B virus X antigen on a preparative scale in *Escherichia coli*, 1997, Journal of Biotechnology, 1997, vol. 56, pp. 81-88.*
Guo et al., Protein tolerance to random amino acid change, (2004) Proc. Natl. Acad. Sci. USA 101: 9205-9210.*
Lazar et al., Trnasforming Growth Factor alpha: Mutation of aspartic Acid 47 and Leucine 48 Results in Different Biological Activities, (1988) Mol. Cell. Biol. 8:1247-1252.*
Hill et al., Functional Analysis of Conserved Histidines in ADP-Glucose Pyrophosphorylase from *Escherichia coli*, (1998) Biochem. Biophys. Res. Comm. 244:573-577.*

(Continued)

*Primary Examiner* — Alexander Kim
(74) *Attorney, Agent, or Firm* — Campbell Nelson Whipps LLC

(57) ABSTRACT

The invention provides methods and nucleic acid constructs to express clostripain. The source of the coding region for recombinantly expressed clostripain is *Clostridium histolyticum*.

18 Claims, 11 Drawing Sheets

OTHER PUBLICATIONS

Whirwam et al., Expression of Fungal Mn Peroxidase in *E. coli* and Refolding to Yield Active Enzyme Biochemical and biophysical Research Communications, vol. 216, Nov. 22, 1995, vol. 216 pp. 1013-1017.*

Tan et al., Cloning, Overexpression, Refolding, and Purification of the Nonspecific Phospholipase C from *Bacillus cereus*, Protein Expression and Purification, 1997, vol. 10, pp. 365-372.*

Dargatz et al., The heterodimeric protease clostripain from *Clostridium histolyticum* is encoded by a single gene., Mol. gen. Genet., 1993, vol. 240, pp. 140-145.*

Witte et al., Clostripain Linker Deletion Variants Yield Active Enzyme in *Escherichia coli*: A Possible Function of the Linker Peptide as Intramolecular Inhibitor of Clostripain Automaturation., Current Microbiology, 1996, vol. 1996, pp. 281-286.* pET11a from Novagen (last veiwed on Sep. 8, 2009).*

Costas et al., Purification and Characterization of a Novel Phosphorous-oxidizing Enzyme from *Pseudomonas stutzeri* WM88, The Journal of Biological Chemistry, 2001, vol. 276, pp. 17429-17436.*

Hart et al., Protein Composition of Vitreoscilla Hemoglobin Inclusion bodies Produced in *Escherichia coli*., The Journal of Biological Chemistry, 1990, vol. 265, pp. 12728-12733.*

Ventura et al., Protein quality in bacterial inclusion bodies., TRENDS in biotechnology, 2006, vol. 24, pp. 179-185.*

Lilie et al., Advanced in refolding of proteins produced in *E. coli*, Current Opinion in biotechnology, 1998, vol. 9, pp. 497-501.*

Dargatz, H. , et al., "The Heterodimeric Protease Clostripain from *Clostridium histolyticum* is Encoded by a Single Gene", *Mol. Gen. Genet.*, 240, (Jul. 1993),140-145.

Witte, V. , et al., "Clostripain Linker Deletion Variants Yeild Active Enzyme in *Escherichia coli*: A Possible Function of the Linker Peptide as Intramolecular Inhibitor of Clostripain Automaturation", *Current Microbiology*, 33, (1996),281-286.

Witte, V. , et al., "Heterologous Expression of the Clostripain Gene from *Clostridium histolyticum* in *Escherichia coli* and *Bacillus subtilis*: Maturation of the Clostripain Precursor is Coupled With Self-Activation", *Microbiology*, 140, (1994),1175-1182.

Sprengart, M. , et al., "The downstream box: an efficient and independent translation Initiation signal in *Escherichia coli*", *EMBO J.*, 15(3), (Feb. 1, 1996),665-74.

Nilsson, J., et al., "Multiple Affinity Domains for the Detection, Purification and Immobilization of Recombinant Proteins", *Journal of Molecular Recognition*, 9 (5/6), 1996, John Wiley & Sons,(Dec. 9, 1996),585-594.

Pop, O., et al., "The Twin-Arginine Signal Peptide of PhoD and the TatAd/Cd Proteins of *Bacillus subtilis* From an Autonomous Tat Translocation System", *Journal of Biological Chemistry*, 277 (5), American Society of Biolochemical Biologists, Birmingham,(Feb. 1, 2002),3268-3273.

Zhan, Y., et al., "Structural Analysis of Regulatory Protein Domains Using GST-Fusion Proteins", *GENE: An International Journal on Genes and Genomes*, 281 (1-2), 2001 Elsevier Science B.V,(Dec. 27, 2001),1-9.

* cited by examiner

Fig. 1A

```
     |Pre sequence ->
     ATG TTA AGA AGA AAA GTA TCA ACA CTA TTA ATG ACA GCT TTG ATA ACT ACT TCA
  1   M   L   R   R   K   V   S   T   L   L   M   T   A   L   I   T   T   S
                                           <-| |Pro sequence ->
     TTT TTA AAT TCC AAA CCC GTA TAT GCA AAT CCA GTA ACT AAA TCC AAG GAT AAT
 19   F   L   N   S   K   P   V   Y   A   N   P   V   T   K   S   K   D   N
                                                               <-| |Light- chain ->
     AAC TTA AAA GAA GTA CAA CAA GTT ACA AGC AAT AAG AGT AAA AAC AAA AAT CAA
 37   N   L   K   E   V   Q   Q   V   T   S   N   K   S   K   N   K   N   Q
     AAA GTA ACT ATT ATG TAC TAT TGC GAC GCA GAT AAC TTG GAA GGA AGT CTA
 55   K   V   T   I   M   Y   Y   C   D   A   D   N   L   E   G   S   L
              EcoRV
     TTA AAT GAT ATC GAG GAA ATG AAA GTT AAA GGA TAT AAG AGT GAT CCT AAT TTA AAT
 73   L   N   D   I   E   E   M   K   T   G   Y   K   S   D   P   N   L   N
     TTA ATT GCT CTT GTA GAC AGA TCC CCA AGA TAT AGC AGT GAA CAC AAT AAA GTT TTA
 91   L   I   A   L   V   D   R   S   P   R   Y   S   S   E   H   N   K   V   L
     GGT GAA GAT TTT AGT AAA AAT GAA TTT CCA GAA CTT CTT AAG ATT AGT ACT TAT GAA
109   G   E   D   F   S   K   N   E   F   P   E   L   L   K   I   S   T   Y   E
                     BamHI
     AGA TTA GAC GGT AAA GAT GAT AGT GAT ACA GAA TTT GAA GTT CTT CTT AAA AAA TAT TCT
127   R   L   D   G   K   D   D   S   D   T   E   F   E   V   L   L   K   K   Y   S
     GCT AAC ATG GGG GAT CCT GAA AAT GCT GAT AAA TAT GTG CTT ATA ATG GCT AAT CAT GGT GGT GCA
145   A   N   M   G   D   P   E   N   A   D   K   Y   V   L   I   M   A   N   H   G   G   A
         |Linker ->                                  <-| |Heavy chain ->
     AAT TAT GAG GCT GAT AAA TAT GTG CTT ATA ATG GCT AAT CAT GGT TGG TGC ATT TGC GAT AGT AAC
163   N   Y   E   A   D   K   Y   V   L   I   M   A   N   H   G   W   C   I   C   D   S   N
     AGG GAA AAA TCA AAT CCA AGA TTA AAT CCA AGA TTA AAT CCA AGA TTA AAT
181   R   E   K   S   N   P   R   L   N   P   R   L   N
```

```
199  CTT GAT AAA AAT GGT GAA GCA GAC TGC CTT TAT ATG GGT GAA ATT TCA GAT CAT
      L   D   K   N   G   E   A   D   C   L   Y   M   G   E   I   S   D   H
217  TTA ACA GAA AAA CAA TCA GTT GAT TTA CTT GCC TTT GAT GCG GAA TGC CTT ATG GGA
      L   T   E   K   Q   S   V   D   L   L   A   F   D   A   E   C   L   M   G
     PstI
235  ACT GCA GAA GTA GCG TAT CAG AGA TAT CAG GGA AAT GGA TTC AAA TCT GCC GAT
      T   A   E   V   A   Y   Q   R   Y   Q   G   N   G   F   K   S   A   D
253  ACT TTA GTT GCT TCA AGC CCA GTA GTT TGG GGT CCT GGA TTC AAA TAT GAT AAG
      T   L   V   A   S   S   P   V   V   W   G   P   G   F   K   Y   D   K
271  ATT TTC GAT AGG ATA AAA GCT AAC ACT GGA GGA ACT AAT GAG GAT GAT TTA ACT
      I   F   D   R   I   K   A   N   T   G   G   T   N   E   D   D   L   T
289  TTA GGT GGT AAA GAA CAA TTT GTA GAA GAG CAA AAT TTT ATT ACC GCC ATT TTA
      L   G   G   K   E   Q   F   V   E   E   Q   N   F   I   T   A   I   L
          HindIII
307  GGT GCA TTA TTT GTA GAA GAG TAT CAA AGA GAC TCA ACA CAT GCC AAT GGT CGC TAT
      G   A   L   F   V   E   E   Y   Q   R   D   S   T   H   A   N   G   R   Y
325  GAT CAA CAC AGC TTT AAT GTT GCT CTA AGT GAT TTA AAG AAA GCT GAA TCA AAA AGA GCC
      D   Q   H   S   F   N   V   A   L   S   D   L   K   K   A   E   S   K   R   A
343  ATA GAT AAT TTA AGA GGA ATT CAT ACA GAT TTA ATG CAT TAC TTC GAT GAA TAT
      I   D   N   L   R   G   I   H   T   D   L   M   H   Y   F   D   E   Y
361  AAA TTA AGA GGA AGT GGA GTT GAA TAT CCT TAT TTT GAC GTG TAT TTA TGT GAA
      K   L   R   G   S   G   V   E   Y   P   Y   F   D   V   Y   L   C   E
379  TCT GAA GGA GAA TGG GTT GAA
      S   E   G   E   W   V   E
```

```
     AAA ATA AAT AAA AGT GAA AAT TTT AGT AGT AAA ACT AAA GAT TTA GCT TCA AAT
397   K   I   N   K   S   E   N   F   S   S   K   T   K   D   L   A   S   N

GCT ATG AAT AAA TTA AAT GAA ATG ATA GTT TAT TCT TTT GGA GAC CCT AGT AAT
415   A   M   N   K   L   N   E   M   I   V   Y   S   F   G   D   P   S   N

AAT TTT AAA GAA GGA AAA AAT GGA TTG AGT ATA TTC TTA CCT AAT GGA GAT AAA
433   N   F   K   E   G   K   N   G   L   S   I   F   L   P   N   G   D   K

AAA TAT TCA ACT TAT TAT ACA TCA ACC AAG ATA CCT CAT TGG ACT ATG CAA AGT
451   K   Y   S   T   Y   Y   T   S   T   K   I   P   H   W   T   M   Q   S

TGG TAT AAT TCA ATA GAT ACA GTT AAA TAT GGA TTG AAT CCT TAC AAA TTA
469   W   Y   N   S   I   D   T   V   K   Y   G   L   N   P   Y   K   L

AGT TGG TGT CTA GAT GGA CAA GAT CCT GAA ATA AAT AAT GTT GGA AAT TGG TTT
487   S   W   C   L   D   G   Q   D   P   E   I   N   N   V   G   N   W   F
             XbaI
                 <-|
     GAA CTT CTA GAT TCT TGG TTT GAT AAA ACT AAT GAT GTA ACT GGA GGA GTT AAT
505   E   L   L   D   S   W   F   D   K   T   N   D   V   T   G   G   V   N
                     XhoI

CAT TAC CAA TGG TAA CTC GAG 3'
523   H   Y   Q   W   *
```

Amino Acid Sequence is SEQ ID NO: 28
Nucleic Acid Sequence is SEQ ID NO: 44

|T7tag ->|                                                        <-| |Light- chain ->
ATG GCT AGC ATG ACT GGT GGA CAG CAA AAT AAT CAA
 M   A   S   M   T   G   G   Q   Q   N   N   Q
                                         51

55  AAA GTA ACT ATT ATG TAC TAT TGC GAC GCA GAT AAT TTG GAA GGA AGT CTA
      K   V   T   I   M   Y   Y   C   D   A   D   N   L   E   G   S   L
              EcoRV

73  TTA AAT GAT ATC GAG GAA ATG AAA ACA GGA TAT AAG GAT AGT CCT AAT TTA AAT
      L   N   D   I   E   E   M   K   T   G   Y   K   D   S   P   N   L   N

91  TTA ATT GCT CTT GTA GAC AGA TCC CCA AGA TAT AGC AGT GAC GAA AAA GTT TTA
      L   I   A   L   V   D   R   S   P   R   Y   S   S   D   E   K   V   L

109  GGT GAA GAT TTT AGT GAT ACA CGT CTT TAT AAG ATT GAA CAC AAT AAG GCA AAT
      G   E   D   F   S   D   T   R   L   Y   K   I   E   H   N   K   A   N

127  AGA TTA GAC GGT AAA AAT GAA TTT CCA GAA GTT CTT TAT AAG TAT GAA
      R   L   D   G   K   N   E   F   P   E   V   L         Y   K   Y   E
                  BamHI

145  GCT AAC ATG GGG GAT CCT GAA GTT CTT AAA TAT GTG CTT AAT AGA TTT ATT GAT TAT TGT AAA TCT
      A   N   M   G   D   P   E   V   L   K   Y   V   L   N   R   F   I   D   Y   C   K   S
                                                <-| |Heavy chain ->

163  AAT TAT GAG GCT GAT AAA TAT GTG CTT AAT AGA TTA ATG GCT AAT CAT GGT GGT GCA
      N   Y   E   A   D   K   Y   V   L   N   R   L   M   A   N   H   G   G   A
     | |Linker ->

181  AGG GAA AAA TCA AAT CCA AGA TTA AAT AGA GCA ATT TGC TGG GAT GAT AGT AAC
      R   E   K   S   N   P   R   L   N   R   A   I   C   W   D   D   S   N

.....526aa

Amino Acid Sequence is SEQ ID NO: 45
Nucleic Acid Sequence is SEQ ID NO: 46

Fig. 2

```
51aa ......
          BamHI
     GCT AAC ATG GGG GAT CCT GAA GTT CTT AAA AAA TTT ATT GAT TAT TGT AAA TCT
145   A   N   M   G   D   P   E   V   L   K   K   F   I   D   Y   C   K   S
                                                                        SacI
     AAT TAT GAG GCT GAT AAA TAT GTG CTT ATA ATG GCT AAT CAT GGT GGT GGA GCT
163   N   Y   E   A   D   K   Y   V   L   I   M   A   N   H   G   G   G   A
     |Linker ->                       <-| |Heavy chain ->
     CAG GAA AAA TCA AAT CCA CAG TTA AAT CAG GCA ATT TGC TGG GAT GAT AGT AAC
181   Q   E   K   S   N   P   Q   L   N   Q   A   I   C   W   D   D   S   N
     CTT GAT AAA AAT GGT GAA GCA GAC TGC CTT TAT ATG GGT GAA ATT TCA GAT CAT
199   L   D   K   N   G   E   A   D   C   L   Y   M   G   E   I   S   D   H
     TTA ACA GAA AAA CAA TCA GTT GAT CAG TAT CTT GCC TTT GAT GCG TGC CTT ATG GGA
217   L   T   E   K   Q   S   V   D   Q   Y   L   A   F   D   A   C   L   M   G
     PstI
     ACT GCA GAA GTA GCG TAT CAG TAT AGA CCA GGT AAT GGA GGA TTT TCT GCC GAT
235   T   A   E   V   A   Y   Q   Y   R   P   G   N   G   G   F   S   A   D
     ACT TTA GTT GCT TCA AGC CCA GTA GTT GGT TGG GGT CCT AAA TAT GAT AAG
253   T   L   V   A   S   S   P   V   V   G   W   G   P   K   Y   D   K
     ATT TTC GAT AGG ATA AAA GAA GTA GGA ACT AAT AAT GAG GAT GAT TTA ACT
271   I   F   D   R   I   K   E   V   G   T   N   N   E   D   D   L   T
     TTA GGT GGT AAA GAA CAA AAC TTT GAT CCT GCA ACC ATT ACC AAT GAG CAA TTA
289   L   G   G   K   E   Q   N   F   D   P   A   T   I   T   N   E   Q   L
```

Fig. 4A

```
307  GGT GCA TTA TTT GTA GAA GAG CAA AGA GAC TCA ACA CAT GCC AAT GGT CGC TAT
      G   A   L   F   V   E   E   Q   R   D   S   T   H   A   N   G   R   Y
                          HindIII 325  GAT CAA CAC TTA AGC TTT TAT GAT TTA AAG AAA GCT GAA TCA GTA AAA AGA GCC
      D   Q   H   L   S   F   Y   D   L   K   K   A   E   S   V   K   R   A 343  ATA GAT AAT TTA GCT GTT AAT CTA AGT AAT GAA AAC AAA AAA TCT GAA ATT GAA
      I   D   N   L   A   V   N   L   S   N   E   N   K   K   S   E   I   E 361  AAA TTA AGA GGA AGT GGA ATT CAT ACA GAT ATG CAT TAC TTC GAT GAA TAT
      K   L   R   G   S   G   I   H   T   D   M   H   Y   F   D   E   Y ..... 526aa
```

Amino Acid Sequence is SEQ ID NO: 47
Nucleic Acid Sequence is SEQ ID NO: 48

Fig. 4B

METHODS AND CONSTRUCTS FOR HIGH YIELD EXPRESSION OF CLOSTRIPAIN

CROSS-REFERENCE TO RELATED APPLICATIONS

This application is a continuation under 35 U.S.C. 111(a) of PCT/US03/16642, filed on May 23, 2003 and published on Dec. 4, 2003 as WO 03/100020 A2, which claims priority under 35 U.S.C 119(e) of U.S. Provisional Application No. 60/383357, filed on May 24, 2002, which applications and publication are incorporated herein by reference.

FIELD OF THE INVENTION

The present invention relates generally to the field of protein expression. More specifically, it relates to DNA constructs for the expression of clostripain.

BACKGROUND OF THE INVENTION

Polypeptides are useful for the treatment of disease in humans and animals. Examples of such polypeptides include insulin for the treatment of diabetes, interferon for treating viral infections, interleukins for modulating the immune system, erythropoietin for stimulating red blood cell formation, and growth factors that act to mediate both prenatal and postnatal growth.

Many bioactive polypeptides can be produced through use of chemical synthesis methods. However, such production methods are often times inefficient and labor intensive which leads to increased cost and lessened availability of therapeutically useful polypeptides. An alternative to chemical synthesis is provided by recombinant technology which allows the high yield production of bioactive polypeptides in microbes. Such production permits a greater number of people to be treated at a lowered cost.

One obstacle to the administration of polypeptides to humans and animals is degradation. Many endogenous proteases exist in humans and animals that rapidly degrade foreign as well as native polypeptides. Degradation by these proteases reduces the effectiveness of therapeutically active polypeptides. One method that may be used to counter the effects of such proteases is to administer polypeptides having increased resistance to proteolytic degradation. Polypeptides having an increased resistance to proteolytic degradation may be produced by replacing a carboxyl group located on the carboxyl-terminus of the polypeptide with an amine group through a process of amidation.

Chemical amidation reactions have been used in the past to change the carboxyl-group to an amide group. Such methods involve the use of expensive and toxic chemicals as well as add a process step during the production of a therapeutically useful polypeptide. This added step reduces the yield of these therapeutically active polypeptides and increases their cost.

An alternative to the use of chemical amidation reactions is use of the protease clostripain. Clostripain (EC 3.4.22.8) is an endopeptidase that cleaves a polypeptide at the carboxyl-terminus of Arg residue. Accordingly, use of clostripain during the production of an amidated therapeutic polypeptide from a precursor polypeptide allows the precurser polypeptide to be cleaved and amidated in the same step to produce a therapeutic polypeptide.

Clostripain is expressed by the anaerobic bacteria *Clostridium histoliticum* and can be isolated from culture filtrates by conventional methods. However, isolation of clostripain from culture filtrates is expensive, inefficient, and is susceptible to contamination by other unwanted proteases that may adversely affect later use of clostripain during production of therapeutic polypeptides. Clostripain has also been expressed and isolated from *Escherichia coli* and *Bacillus subtilis*. However, these attempts produced low yields of clostripain that was of low enzymatic activity.

The ability to efficiently produce active clostripain on a large scale would allow for the more efficient production of therapeutic polypeptides at a lessened cost. Accordingly, a need exists for efficient production methods to produce clostripain.

SUMMARY OF THE INVENTION

The invention provides an expression cassette containing a promoter that is operably linked to an open reading frame that encodes a tag that is operably linked to clostripain or a variant of clostripain. The invention also provides a nucleic acid construct containing a vector and the expression cassette of the invention. A cell containing the expression cassette of the invention is also provided. The invention provides a cell containing the nucleic acid construct of the invention. A method to overproduce clostripain is also provided by the invention. An RNA transcript produced by transcription of the expression cassette of the invention is provided. Accordingly, a polypeptide produced by translation of the RNA transcript of the invention is also provided. Also provided by the invention is an expression cassette containing a promoter that is operably linked to an open reading frame that encodes an inclusion body fusion protein that is operably linked to clostripain or a variant of clostripain. The invention also provides an expression cassette containing a promoter that is operably linked to an open reading frame that encodes an inclusion body fusion partner that is operably linked to a cleavable peptide linker that is operably linked to clostripain or a variant of clostripain. Also provided is a nucleic acid construct containing a vector and the expression cassette that encodes an operably linked inclusion body fusion partner. A cell containing an expression cassette that encodes an operably linked inclusion body fusion partner is also provided. A cell containing a nucleic acid construct that encodes an operably linked inclusion body fusion partner is provided by the invention. The invention also provides a eukaryotic expression cassette that includes a eukaryotic promoter operably linked to an open reading frame that encodes clostripain. Further provided is a eukaryotic nucleic acid construct containing a vector and a eukaryotic expression cassette of the invention. The invention also provides a cell containing the eukaryotic expression cassette of the invention. A cell containing the eukaryotic nucleic acid construct of the invention is also provided. An RNA transcript produced by transcription of the eukaryotic expression cassette of the invention is provided. Accordingly, a polypeptide produced by translation of the RNA transcript from a eukaryotic expression cassette of the invention is also provided.

The invention provides an expression cassette containing a promoter that is operably linked to an open reading frame that encodes a tag that is operably linked to clostripain. Preferably the promoter is a constituitive promoter. More preferably the promoter is a regulatable promoter. Even, more preferably the promoter is an inducible promoter. Most preferably the promoter is a tac promoter. Preferably the tag increases the production of clostripain by a cell. More preferably the tag has an amino acid sequence having at least 70% sequence identity to SEQ ID NO: 17. More preferably the tag has an amino acid sequence having at least 80% sequence identity to SEQ ID NO: 17. Even more preferably the tag has an amino acid sequence having at least 90% sequence identity to SEQ ID NO: 17. Still even more preferably the tag has an amino acid sequence having at least 98% sequence identity to SEQ ID NO: 17. Most preferably the tag has an amino acid sequence corresponding to SEQ ID NO: 17. Preferably the open reading frame encodes a variant of clostripain having at least 70% amino acid sequence identity to SEQ ID NO: 29. More preferably the open reading frame encodes a variant of clostripain having at least 80% amino acid sequence identity to SEQ ID NO: 29. Even more preferably the open reading frame encodes a variant of clostripain having at least 90% amino acid sequence identity to SEQ ID NO: 29. Still even more preferably the open reading frame encodes a variant of clostripain having at least 98% amino acid sequence identity to SEQ ID NO: 29. Most preferably the open reading frame encodes clostripain having an amino acid sequence corresponding to SEQ ID NO: 29. The expression cassette of the invention can also include an operator sequence that is operably linked to the promoter that is operably linked to the open reading frame encoding clostripain. Preferably the operator sequence is a bacterial operator sequence. More preferably the operator sequence is obtained from a gene involved in sugar metabolism. Most preferably the operator sequence is the lac operator sequence. The expression cassette of the invention can also encode an inclusion body fusion partner that is operably linked to the open reading frame encoding clostripain. Preferably the inclusion body fusion partner has an amino acid sequence having at least 70% amino acid sequence identity to any one of SEQ ID NOs: 1-16. More preferably the inclusion body fusion partner has an amino acid sequence having at least 80% amino acid sequence identity to any one of SEQ ID NOs: 1-16. Even more preferably the inclusion body fusion partner has an amino acid sequence having at least 90% amino acid sequence identity to any one of SEQ ID NOs: 1-16. Still even more preferably the inclusion body fusion partner has an amino acid sequence having at least 98% amino acid sequence identity to any one of SEQ ID NOs: 1-16. Most preferably the inclusion body fusion partner has an amino acid sequence corresponding to any one of SEQ ID NOs: 1-16.

The invention also provides a nucleic acid construct containing a vector and an expression cassette of the invention. Preferably the vector is a phagemid, cosmid, f-factor, virus, bacteriophage, yeast artificial chromosome, or bacterial artificial chromosome. More preferably the vector is a plasmid.

The invention provides a cell containing a nucleic acid construct of the invention. Preferably the cell is a eukaryotic cell. More preferably the eukaryotic cell is a mammalian cell. Even more preferably the eukaryotic cell is a yeast cell. Most preferably the eukaryotic cell is an insect cell. More preferably the cell is a prokaryotic cell. Even more preferably the prokaryotic cell is a bacterium. Still even more preferably the prokaryotic cell is an *Escherichia coli*. Most preferably the prokaryotic cell is *Escherichia coli* BL21.

The invention provides a cell containing an expression cassette of the invention. Preferably the cell is a eukaryotic cell. More preferably the eukaryotic cell is a mammalian cell. Even more preferably the eukaryotic cell is a yeast cell. Most preferably the eukaryotic cell is an insect cell. More preferably the cell is a prokaryotic cell. Even more preferably the prokaryotic cell is a bacterium. Still even more preferably the prokaryotic cell is an *Escherichia coli*. Most preferably the prokaryotic cell is *Escherichia coli* BL21.

Also provided by the invention is a eukaryotic expression cassette containing a eukaryotic promoter operably linked to an open reading frame that encodes clostripain. Also provided by the invention is a eukaryotic expression cassette containing a eukaryotic promoter operably linked to an open reading frame that encodes a variant of clostripain. Preferably the eukaryotic promoter is a constituitive promoter. More preferably the eukaryotic promoter is a regulatable promoter. Even more preferably the eukaryotic promoter is an inducible promoter. Most preferably the eukaryotic promoter is a GAL1 promoter. Preferably the open reading frame encodes a variant of clostripain having at least 70% amino acid sequence identity to SEQ ID NO: 29. More preferably the open reading frame encodes a variant of clostripain having at least 80% amino acid sequence identity to SEQ ID NO: 29. Even more preferably the open reading frame encodes a variant of clostripain having at least 90% amino acid sequence identity to SEQ ID NO: 29. Still even more preferably the open reading frame encodes a variant of clostripain having at least 98% amino acid sequence identity to SEQ ID NO: 29. Most preferably the open reading frame encodes clostripain having an amino acid sequence corresponding to SEQ ID NO: 29. Preferably the eukaryotic expression cassette encodes an enhancer that is operably linked to the open reading frame that encodes clostripain. Preferably the enhancer is a transcriptional enhancer. More preferably the enhancer is a GAL4 or SV40 early gene enhancer. Preferably the eukaryotic expression cassette encodes a signal sequence that is operably linked to the open reading frame that encodes clostripain. Preferably the signal sequence is a secretion signal. More preferably the signal sequence is from α-factor. The eukaryotic expression cassette of the invention can also encode an inclusion body fusion partner that is operably linked to the open reading frame that encodes clostripain. Preferably the inclusion body fusion partner has an amino acid sequence having at least 70% amino acid sequence identity to any one of SEQ ID NOs: 1-16. More preferably the inclusion body fusion partner has an amino acid sequence having at least 80% amino acid sequence identity to any one of SEQ ID NOs: 1-16. Even more preferably the inclusion body fusion partner has an amino acid sequence having at least 90% amino acid sequence identity to any one of SEQ ID NOs: 1-16. Still even more preferably the inclusion body fusion partner has an amino acid sequence having at least 98% amino acid sequence identity to any one of SEQ ID NOs: 1-16. Most preferably the inclusion body fusion partner has an amino acid sequence corresponding to any one of SEQ ID NOs: 1-16.

The invention also provides a nucleic acid construct containing a vector; and a eukaryotic expression cassette of the invention. Preferably the vector is a plasmid, virus, yeast artificial chromosome, or a shuttle vector. More preferably the vector is a plasmid. Most preferably the vector is a virus.

The invention provides a cell containing a eukaryotic nucleic acid construct of the invention. Preferably the cell is a eukaryotic cell. More preferably the eukaryotic cell is a mammalian cell. Even more preferably the eukaryotic cell is a yeast cell. Most preferably the eukaryotic cell is an insect cell. The cell may be a prokaryotic cell. Preferably the prokaryotic cell is a bacterium. More preferably the prokaryotic cell is an *Escherichia coli*. Most preferably the prokaryotic cell is *Escherichia coli* BL21.

The invention provides a cell containing a eukaryotic expression cassette of the invention. Preferably the cell is a eukaryotic cell. More preferably the eukaryotic cell is a mammalian cell. Even more preferably the eukaryotic cell is a yeast cell. Most preferably the eukaryotic cell is an insect cell. The cell may be a prokaryotic cell. Preferably the prokaryotic cell is a bacterium. More preferably the prokaryotic cell is an *Escherichia coli*. Most preferably the prokaryotic cell is *Escherichia coli* BL21.

Definitions

Abbreviations: IPTG: isopropylthio-β-D-galactoside; PCR: polymerase chain reaction; mRNA: messenger ribonucleic acid; DNA: deoxyribonucleic acid; RNA: ribonucleic acid; FLAG: hydrophilic 8-amino acid peptide (DYKD-DDDK) (SEQ ID NO: 25).

The term "Altered isoelectric point" refers to changing the amino acid composition of an inclusion body fusion partner to effect a change in the isoelectric point of clostripain or a variant thereof that is operably linked to the inclusion body fusion partner.

An "Amino acid analog" includes amino acids that are in the D rather than L form, as well as other well known amino acid analogs, e.g., N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4, -tetrahydroisoquinoline -3-carboxylic acid, penicillamine, ornithine, citruline, N -methyl-alanine, para-benzoyl-phenylalanine, phenylglycine, propargylglycine, sarcosine, N-acetylserine, N-formylmethionine, 3-methyl-histidine, 5-hydroxylysine, norleucing, norvaline, orthonitro-phenylglycine, and other similar amino acids.

The terms, "cells," "cell cultures", "Recombinant host cells", "host cells", and other such terms denote, for example, microorganisms, insect cells, and mammalian cells, that can be, or have been, used as recipients for nucleic acid constructs or expression cassettes, and include the progeny of the original cell which has been transformed. It is understood that the progeny of a single parental cell may not necessarily be completely identical in morphology or in genomic or total DNA complement as the original parent, due to natural, accidental, or deliberate mutation. Many cells are available from ATCC and commercial sources. Many mammalian cell lines are known in the art and include, but are not limited to, Chinese hamster ovary (CHO) cells, HeLa cells, baby hamster kidney (BHK) cells, monkey kidney cells (COS), and human hepatocellular carcinoma cells (e.g., Hep G2). Many prokaryotic cells are known in the art and include, but are not limited to, *Escherichia coli* and *Salmonella typhimurium*. Sambrook and Russell, Molecular Cloning: A Laboratory Manual, 3rd edition (Jan. 15, 2001) Cold Spring Harbor Laboratory Press, ISBN: 0879695765. Many insect cells are known in the art and include, but are not limited to, silkworm cells and mosquito cells. (Franke and Hruby, *J. Gen. Virol.*, 66:2761 (1985); Marumoto et al., *J. Gen. Virol.*, 68:2599 (1987)).

A "Cleavable peptide linker" refers to a peptide sequence having a cleavage recognition sequence. A cleavable peptide linker can be cleaved by an enzymatic or a chemical cleavage agent. Numerous peptide sequences are known that are cleaved by enzymes or chemicals. Harlow and Lane, Antibodies: A Laboratory Manual, Cold Spring Harbor Laboratory Press, Cold Spring Harbor, N.Y. (1988); Walsh, Proteins Biochemistry and Biotechnology, John Wiley & Sons, LTD., West Sussex, England (2002).

A "Coding sequence" is a nucleic acid sequence which is translated into a polypeptide, such as a preselected polypeptide, usually via mRNA. The boundaries of the coding sequence are determined by a translation start codon at the 5'-terminus and a translation stop codon at the 3'-terminus of an mRNA. A coding sequence can include, but is not limited to, cDNA, and recombinant nucleic acid sequences.

A "Conservative amino acid" refers to an amino acid that is functionally similar to a second amino acid. Such amino acids may be substituted for each other in a polypeptide with a minimal disturbance to the structure or function of the polypeptide according to well known techniques. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine M), Cysteine (C); Basic: Arginine (R), Lysine (K), Histidine (H); Acidic: Aspartic acid (I), Glutamic acid (E), Asparagine (N), Glutamine (Q).

"Constitutive promoter" refers to a promoter that is able to express a gene or open reading frame without additional regulation. Such constitutive promoters provide constant expression of operatively linked genes or open reading frames under nearly all conditions.

An "enhancer" is a DNA sequence which can stimulate promoter activity and may be an innate element of the promoter or a heterologous element inserted to enhance the expression level of a promoter. An enhancer is capable of operating in both orientations (normal or flipped), and is capable of functioning even when moved either upstream or downstream from the promoter.

A "eukaryotic promoter" is a promoter sequence that is operable in a eukaryotic cell. Examples of eukaryotic promoters include, but are not limited to, a baculovirus promoter, a yeast promoter, an SV40 early promoter, a mouse mammary tumor virus LTR promoter, and a herpes simplex promoter. Many eukaryotic promoters are also tissue specific promoters in that they are more active in one type of tissue than in another tissue type.

An "Expression cassette" as used herein means a DNA sequence capable of directing expression of a particular polynucleotide sequence in an appropriate host cell, comprising a promoter operably linked to the polynucleotide sequence of interest which is operably linked to termination signals. It also typically comprises sequences required for proper translation of the nucleotide sequence. The coding region (open reading frame) codes for clostripain or a variant of clostripain. The expression cassette comprising the open reading frame may be chimeric, meaning that at least one of its components is heterologous with respect to at least one of its other components. The expression cassette may also be one which is naturally occurring but has been obtained in a recombinant form useful for heterologous expression. The expression of the nucleotide sequence (open reading frame) in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

The term "Gene" is used broadly to refer to any segment of nucleic acid that encodes clostripain or a variant thereof. Thus, a gene may include a coding sequence for clostripain and/or the regulatory sequences required for expression. A gene encoding clostripain may also be optimized for expression in a given organism. For example, a codon usage table may be used to optimize the gene for expression in *Escherichia coli*. Harlow and Lane, Antibodies: A Laboratory Manual, Cold Spring Harbor Laboratory Press, Cold Spring Harbor, N.Y. (1988).

An "Inclusion body" is an amorphous deposit in the cytoplasm of a cell; an aggregated protein appropriate to the cell but damaged, improperly folded or liganded, or a similarly inappropriately processed foreign protein, such as a viral coat protein or recombinant DNA product.

An "Inclusion body fusion partner" (IBFP) is an amino acid sequence having SEQ ID NO: 1-16, or variants thereof, that cause a clostripain or a variant of clostripain that is operably linked to the inclusion body fusion partner to form an inclusion body when expressed within a cell. The inclusion body fusion partners of the invention can be altered to confer isolation enhancement onto an inclusion body that contains the altered inclusion body fusion partner. Examples of inclusion body fusion partners are provided in Table I.

"Inducible promoter" refers to those regulated promoters that can be turned on by an external stimulus (e.g. a chemical, nutritional stress, or heat). For example, the lac promoter can be induced through use of IPTG (isopropylthio-β-D-galactoside). In another example, the bacteriophage lambda $P_L$ promoter can be regulated by the temperature-sensitive repressor, cIts857 which represses $P_L$ transcription at low temperatures but not at high temperatures. Thus, temperature shift may be used to induce transcription from the $P_L$ promoter. Sambrook and Russell, Molecular Cloning: A Laboratory Manual, 3rd edition (Jan. 15, 2001) Cold Spring Harbor Laboratory Press, ISBN: 0879695765.

The term "Isolation enhancement" refers to the alteration of characteristics of an inclusion body that aids in purification of a clostripain or variant of clostripain that is operably linked to the inclusion body fusion partner. For example, alteration of an inclusion body fusion partner to increase the solubility of an inclusion body formed from clostripain or a variant of clostripain that is operably linked to an inclusion body fusion partner would be isolation enhancement. In another example, alteration of an inclusion body fusion partner to control the solubility of an inclusion body at a select pH would be isolation enhancement.

A "nucleic acid construct" is a vector into which an expression cassette has been inserted. For example, a nucleic acid construct can be a plasmid containing an expression cassette of the invention. In another example, a nucleic acid construct can be a virus into which an expression cassette of the invention has been inserted.

An "open reading frame" (ORF) is a region of a nucleic acid sequence that encodes a polypeptide, such as clostripain; this region may represent a portion of a coding sequence or a total coding sequence.

"Operably-linked" refers to the association of nucleic acid sequences or amino acid sequences on a single nucleic acid fragment or a single amino acid sequence so that the function of one is affected by the other. For example, a regulatory DNA sequence is said to be "operably linked to" or "associated with" a DNA sequence that codes for an RNA if the two sequences are situated such that the regulatory DNA sequence affects expression of the coding DNA sequence (i.e., that the coding sequence is under the transcriptional control of the promoter). In an example related to amino acid sequences, an inclusion body fusion partner is said to be operably linked to clostripain when the inclusion body fusion partner causes the linked clostripain or variant of clostripain to form an inclusion body. In another example, a signal sequence is said to be operably linked to clostripain when the signal sequence directs the linked clostripain to a specific location in a cell or promotes secretion of the linked clostripain from the cell.

An "Operator" is a site on DNA at which a repressor protein binds to prevent transcription from initiating at the adjacent promoter. Many operators and repressors are known and may be exemplified by the lac operator and the lac repressor. Lewin, Genes VII, Oxford University Press, New York, N.Y. (2000).

The term "polypeptide" refers to a polymer of amino acids, thus, peptides, oligopeptides, and proteins are included within the definition of polypeptide. This term optionally includes post expression modifications of the polypeptide, for example, glycosylations, acetylations, phosphorylations and the like. Included within the definition are, for example, polypeptides containing one or more analogues of an amino acid or labeled amino acids. Examples of rabiolabeled amino acids include, but are not limited to, $S^{35}$-methionine, $S^{35}$-cysteine, $H^3$-alanine, and the like. The invention may also be used to produce deuterated polypeptides by growing cells that express the polypeptide in deuterium. Such deuterated polypeptides are particularly useful during NMR studies.

"Promoter" refers to a nucleotide sequence, usually upstream (5') to its coding sequence, which controls the expression of the coding sequence by providing the recognition site for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus one or more regulatory elements that are capable of controlling the expression of a coding sequence. Promoters may be derived in their entirety from a native gene, or be composed, of different elements derived from different promoters found in nature, or even be comprised of synthetic DNA segments. A promoter may also contain DNA sequences that are involved in the binding of protein factors which control the effectiveness of transcription initiation in response to physiological or environmental conditions.

The term "Purification stability" refers to the isolation characteristics of an inclusion body formed from clostripain or a variant of clostripain that is operably linked to an inclusion body fusion partner. High purification stability indicates that an inclusion body is able to be isolated from a cell in which it was produced. Low purification stability indicates that the inclusion body is unstable during purification due to dissociation of the linked clostripain or variant of clostripain forming the inclusion body.

"Purified" and "isolated" mean, when referring to a polypeptide or nucleic acid sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

"Regulated promoter" refers to a promoter that directs gene expression in a controlled manner rather than in a constitutive manner. Regulated promoters include inducible promoters and repressible promoters. Such promoters may include natural and synthetic sequences as well as sequences that may be a combination of synthetic and natural sequences. Different promoters may direct the expression of a gene in response to different environmental conditions. Typical regulated promoters useful in the invention include, but are not limited to, promoters used to regulate metabolism (e.g. an IPTG-inducible lac promoter) heat-shock promoters (e.g. an SOS promoter), and bacteriophage promoters (e.g. a T7 promoter).

A "Ribosome binding site" is a DNA sequence that encodes a site on an mRNA at which the small and large subunits of a ribosome associate to form an intact ribosome and initiate translation of the mRNA. Ribosome binding site consensus sequences include AGGA or GAGG and are usually located some 8 to 13 nucleotides upstream (5') of the initiator AUG codon on the mRNA. Many ribosome binding sites are known in the art. (Shine et al., *Nature*, 254: 34, (1975); Steitz et al., "Genetic signals and nucleotide sequences in messenger RNA", in: Biological Regulation and Development: Gene Expression (ed. R. F. Goldberger) (1979)).

The term "Self-adhesion" refers to the association between individual polypeptides, that have an inclusion body fusion partner operably linked to clostripain, to form an inclusion body. Self-adhesion affects the purification stability of an inclusion body formed from the linked clostripain. Self-adhesion that is too great produces inclusion bodies containing clostripain that are so tightly associated with each other that it is difficult to separate individual clostripain molecules from an isolated inclusion body. Self-adhesion that is too low produces inclusion bodies that are unstable during isolation due to dissociation of the clostripain molecules that form the inclusion body. Self-adhesion can be regulated by altering the amino acid sequence of an inclusion body fusion partner.

A "Signal sequence" is a region in a protein or polypeptide responsible for directing an operably linked polypeptide to a cellular location, compartment, or secretion from the cell as designated by the signal sequence. For example, signal sequences direct operably linked polypeptides to the inner membrane, periplasmic space, and outer membrane in bacteria. The nucleic acid and amino acid sequences of such signal sequences are well known in the art and have been reported. Watson, Molecular Biology of the Gene, 4th edition, Benjamin/Cummings Publishing Company, Inc., Menlo Park, Calif. (1987); Masui et al., in: Experimental Manipulation of Gene Expression, (1983); Ghrayeb et al., *EMBO J.,* 3: 2437 (1984); Oka et al., *Proc. Natl. Acad. Sci. USA,* 82: 7212 (1985); Palva et al., *Proc. Natl. Acad. Sci. USA,* 79: 5582 (1982); U.S. Pat. No. 4,336,336).

Signal sequences, preferably for use in insect cells, can be derived from genes for secreted insect or baculovirus proteins, such as the baculovirus polyhedrin gene (Carbonell et al., *Gene,* 73:409 (1988)). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, signal sequences of non-insect origin, such as those derived from genes encoding human α-interferon (Maeda et al., *Nature,* 315:592 (1985)), human gastrin-releasing peptide (Lebacq-Verheyden et al., *Mol. Cell. Biol.,* 8: 3129 (1988)), human IL-2 (Smith et al., *Proc. Natl. Acad. Sci. USA,* 82: 8404 (1985)), mouse IL-3 (Miyajima et al., *Gene* 58: 273 (1987)) and human glucocerebrosidase (Martin et al., *DNA* 7: 99 (1988)), can also be used to provide for secretion in insects.

Suitable yeast signal sequences can be derived from genes for secreted yeast proteins, such as the yeast invertase gene (EPO Publ. No. 012 873; JPO Publ. No. 62,096,086) and the A-factor gene (U.S. Pat. No. 4,588,684). Alternatively, sequences of non-yeast origin, such as from interferon, exist that also provide for secretion in yeast (EPO Publ. No. 060 057).

The term "Solubility" refers to the amount of a substance that can be dissolved in a unit volume of solvent. For example, solubility as used herein refers to the ability of clostripain to be resuspended in a volume of solvent, such as a biological buffer.

A "Tag" refers to an amino acid sequence that is operably linked to a peptide or protein. Such tag sequences may provide for the increased expression of a desired peptide or protein. Such tag sequences may also form a cleavable peptide linker when they are operably linked to another peptide or protein. An example of a tag sequence includes, but is not limited to, the sequence indicated in SEQ ID NO: 17.

A "Transcription terminator sequence" is a signal within DNA that functions to stop RNA synthesis at a specific point along the DNA template. A transcription terminator may be either rho factor dependent or independent. An example of a transcription terminator sequence is the T7 terminator. Transcription terminators are known in the art and may be isolated from commercially available vectors according to recombinant methods known in the art. (Sambrook and Russell, Molecular Cloning: A Laboratory Manual, 3rd edition (Jan. 15, 2001) Cold Spring Harbor Laboratory Press, ISBN: 0879695765; Stratagene, La Jolla, Calif.).

"Transformation" refers to the insertion of an exogenous nucleic acid sequence into a host cell, irrespective of the method used for the insertion. For example, direct uptake, transduction, f-mating or electroporation may be used to introduce a nucleic acid sequence into a host cell. The exogenous nucleic acid sequence may be maintained as a non-integrated vector, for example, a plasmid, or alternatively, may be integrated into the host genome.

A "Translation initiation sequence" refers to a DNA sequence that codes for a sequence in a transcribed mRNA that promotes efficient translation of an mRNA Numerous translation initiation sequences are known in the art. These sequences are sometimes referred to as leader sequences. A translation inititation sequence may include an optimized ribosome binding site. In the present invention, bacterial translational initiation sequences are preferred. Such translation initiation sequences are well known in the art and can be obtained from, but are not limited to, bacteriophage T7, bacteriophage ϕ10, and the gene encoding ompT. Those of skill in the art can readily obtain and clone translation initiation sequences from a variety of commercially available plasmids, such as the pET (plasmid for expression of T7 RNA polymerase) series of plasmids. (Novagen, Madison, Wis.). Examples of translation initiation sequences are provided in Table I. Those of skill in the art realize that many translation initiation sequences can be used according to the invention.

A "variant" of clostripain is a polypeptide derived from native clostripain by deletion or addition of one or more amino acids to the N-terminal and/or C-terminal end of the native polypeptide; deletion or addition of one or more amino acids at one or more sites in the native protein; or substitution of one or more amino acids at one or more sites in the native protein. Such substitutions or insertions are preferably conservative amino acid substitutions. Also, a variant of clostripain will exhibit a detectable amount of protease activity. Methods for such manipulations are generally known in the art. (Kunkel, *Proc. Natl. Acad. Sci. USA,* 82:488, (1985); Kunkel et al., *Methods in Enzymol.,* 154:367 (1987); U.S. Pat. No. 4,873,192; Walker and Gaastra, eds. (1983) *Techniques in Molecular Biology* (MacMillan Publishing Company, New York)) and the references cited therein. Also, kits are commercially available for mutating. DNA (Quick change Kit, Stratagene, La Jolla, Calif.). Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.). An example of a variant of clostripain is a linker deletion variant in which the nonapeptide linker that connects the light chain from the heavy chain in the native enzyme has been deleted.

A "Vector" includes, but is, not limited to, any plasmid, cosmid, bacteriophage, yeast artificial chromosome, bacterial artificial chromosome, f-factor, phagemid or virus in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication).

Specifically included are shuttle vectors by which are DNA vehicles capable, naturally or by design, of replication in two different host organisms (e.g. bacterial, mammalian, yeast or insect cells).

BRIEF DESCRIPTION OF THE DRAWINGS

FIGS. 1A-1C shows the open reading frame of cloned prepro-clostripain (1-526). The pre-sequence, pro-sequence, light-chain, and heavy-chain are indicated by bracketed lines. Individual restriction enzyme recognition sites are also indicated.

FIG. 2 shows the N-terminal sequence of the cloned T7tag-clostripain (51-526). The T7tag sequence, linker sequence, and the amino-terminus of the clostripain heavy-chain are indicated by bracketed lines. Individual restriction enzyme recognition sites are also indicated.

FIGS. 4A-4B shows the sequences and positions of the mutations in the nonapeptide linker region.

DETAILED DESCRIPTION OF THE INVENTION

Figure 3:
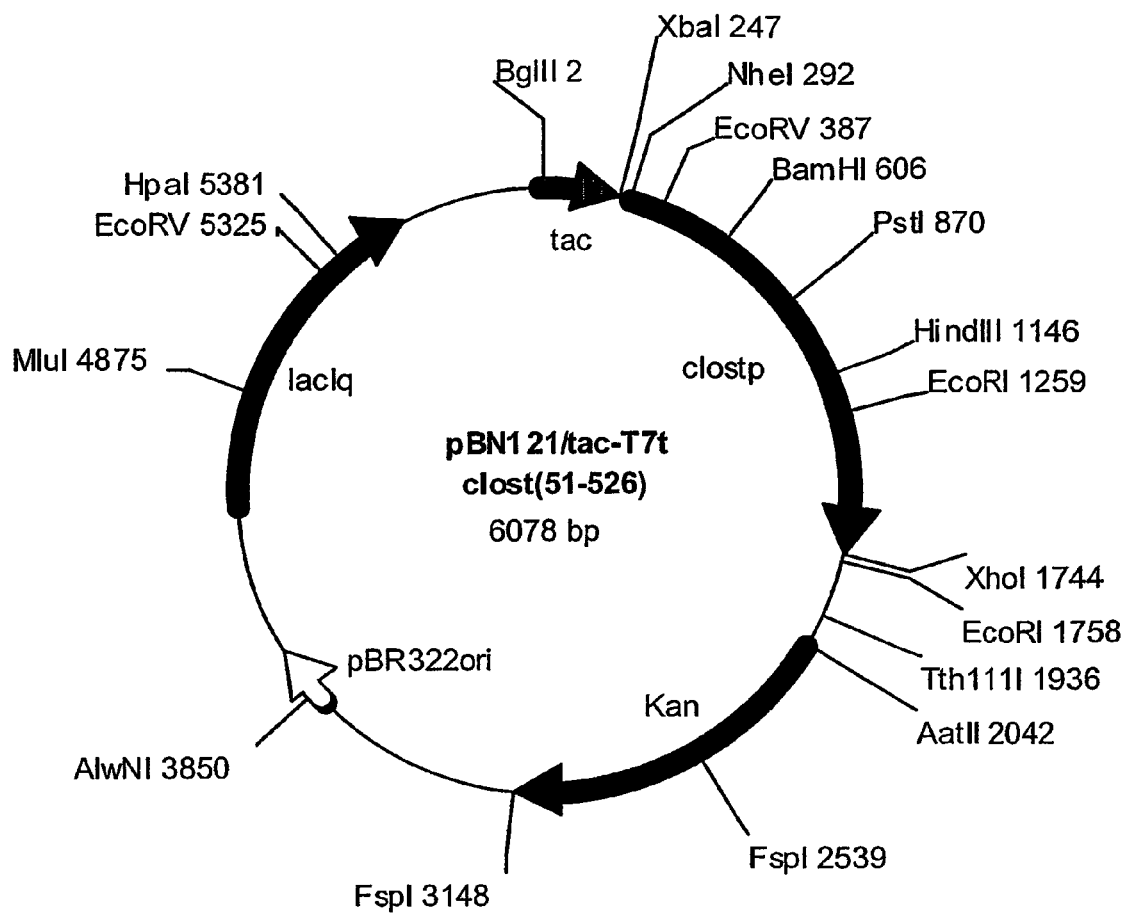
FIG. 3 is a plasmid map of the pBN121 (Tac)-T7tag-Clost (51-526) expression vector. pBR322ori=pBR322 replication origin; lacIq=lac repressor gene; kan=kanamycin resistance gene; tac=tac promoter, clostp=T7tag-clostripain gene.
Figure 5:
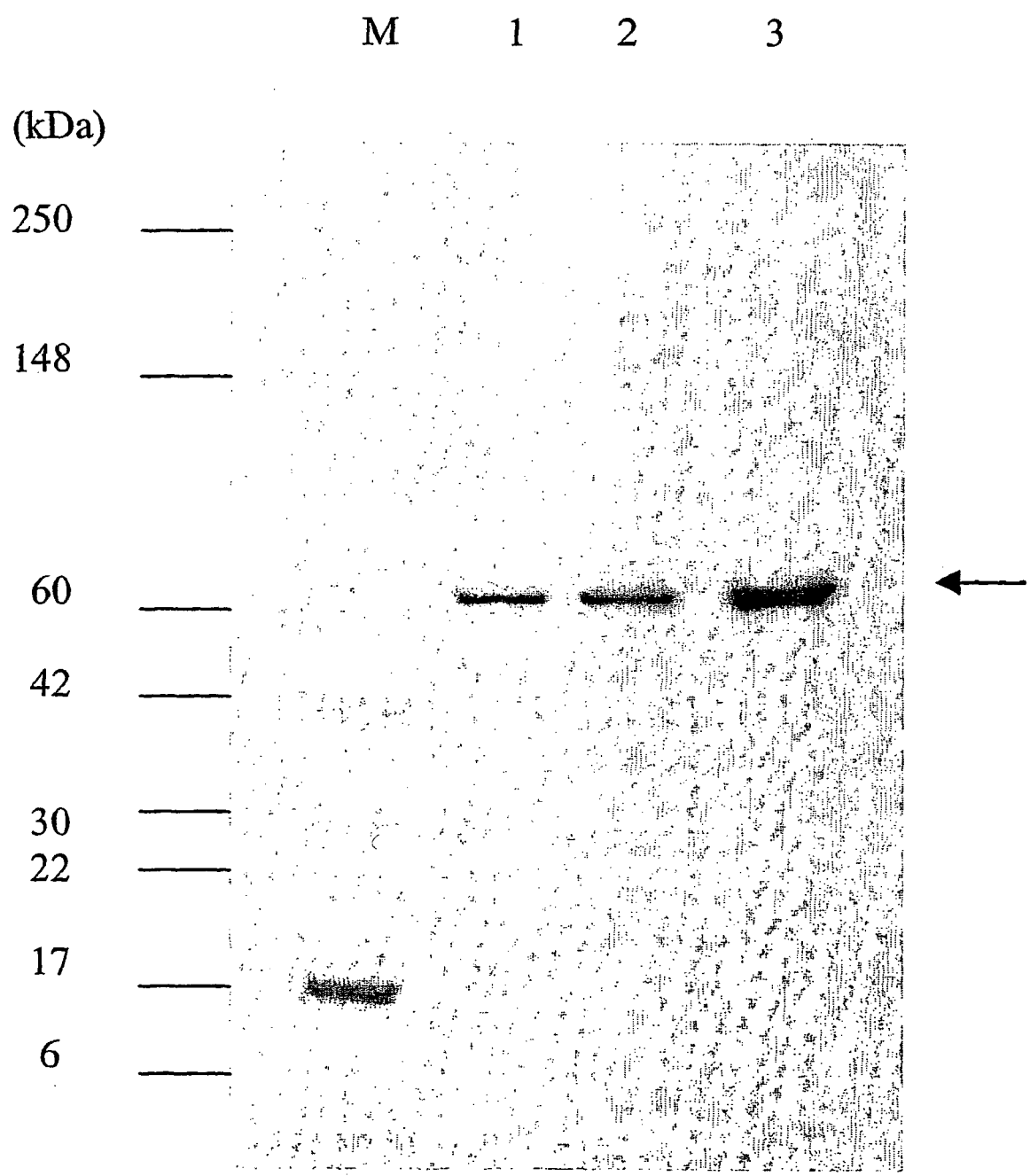
FIG. 5 illustrates an SDS-PAGE (4-20% Tris-Glycine gel) analysis of recombinant clostripain core proteins T7tag-clostripain(51-526) and clostripain(51-526) expressed in E. coli strain BL21. The position of the recombinant clostripain protein is indicted by an arrow. Bacterial cells harboring pBN121 (Tac)-T7tag-clost(51-526) or pBN121 (Tac)-clos(51-526) were induced and harvested 4 hr after induction. Cells were lysed and the inclusion bodies, isolated by centrifugation were boiled in SDS sample buffer. Lane M: molecular weight markers, as indicated (kDa). Lanes 1, 2: clostripain(51-526) from two different isolates. Lane 3: T7tag-clostripain(51-526). The gel was stained with Coomassie blue.
Figure 6:
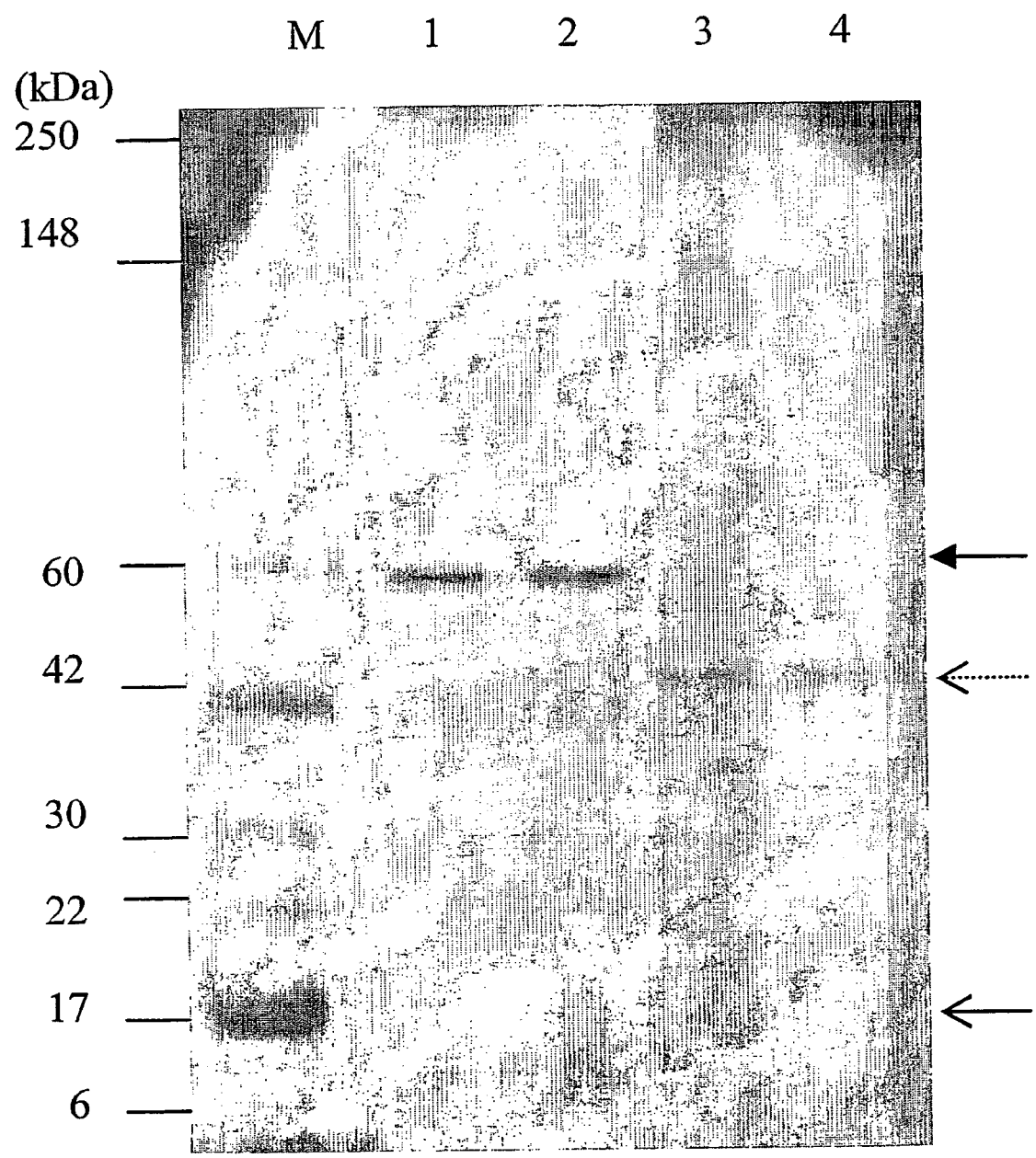
FIG. 6 illustrates an SDS-PAGE (4-20% Tris-Glycine gel) analysis of in vitro processing of clostripain core protein T7tag-clostripain(51-526). Lane M: molecular weight markers, as indicated (kDa). Lanes 1 and 2: T7tag-clostripain(51-526) before activation in 2M urea. Lanes 3 and 4: T7tag-clostripain(51-526) after activation in activation buffer containing 2 M urea at room temperature for 1 hr. The gel was stained with Coomassie blue. The bold arrow indicates the position of the T7tag-clostripain(51-526) before activation. The dotted arrow and light arrow indicate the positions of clostripain subunits following activation.
Figure 7:
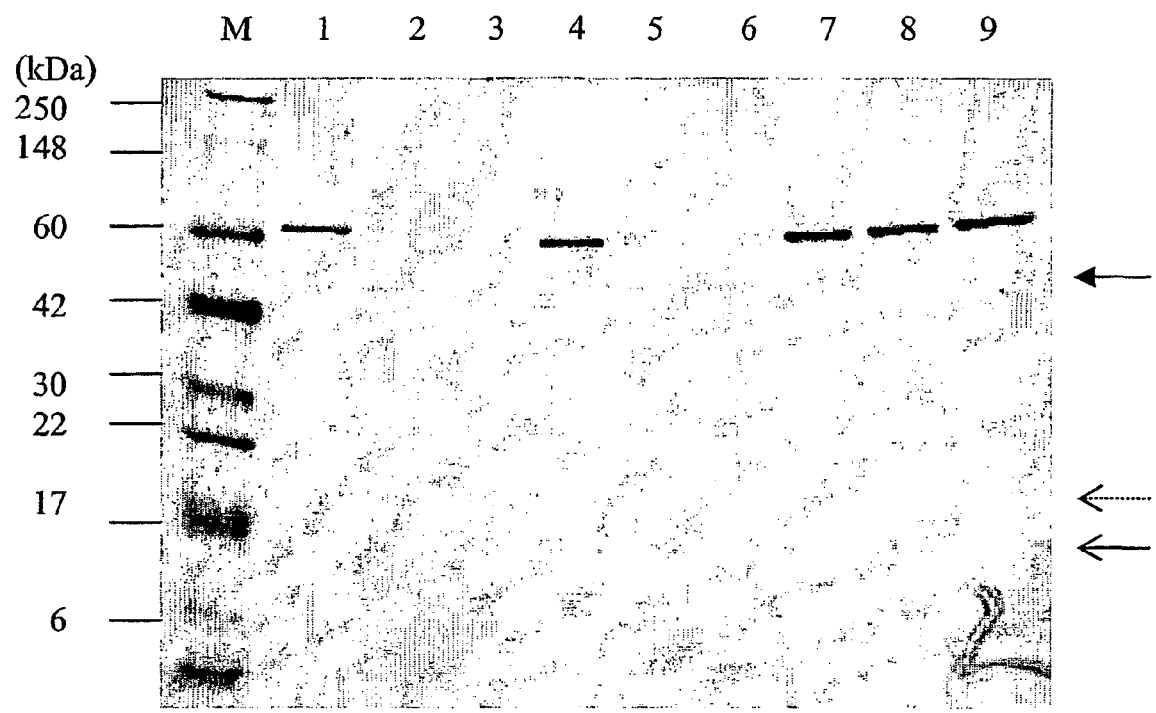
FIG. 7 shows a comparison of in vitro processing of clostripain proenzyme, core protein, and core protein mutant containing linker mutations. Inclusion bodies were extracted from 0.15 $OD_{600}$ of IPTG-induced cells. Lane 1: molecular weight marker. Lanes 2-4: clostripain proenzyme from pET23a-proclos(28-526)/HMS174DE3. Lanes 5-7: clostripain core protein from pET23a-Clos(51-526)/HMS174 (DE3). Lanes 8-9: pET23a-Clos(51-526, R181Q, R187Q, R190Q)/HMS174(DE3). After solubilization in 8 M urea, proteins were activated in activation buffer containing 2 M urea for 0 min (lanes 2, 5, 8), 20 min (lanes 3, 6, 9), or 60 min (lanes 4, 7, 10). Proteins were then loaded on to a 4-20% Tris-Glycine SDS gel for electrophoresis. The protein bands were detected by Coomassie blue staining. Banding positions of clostripain subunits are indicated by arrows: (bold arrow) heavy chain, (dotted arrow) light chain from Mclost(28-526), (light arrow) light chain from Mclost(51-526). Protein molecular weight markers are indicated in kDa (lane FIG. 8 shows an SDS-PAGE (4-20% Tris-Glycine gel) analysis of recombinant clostripain linker deletion mutant clostripain (51-526, Δ [182-190], R181Q) expressed in E. coli strain BL21(DE3) and BL21(DE3)pLysS. Bacteria harboring pET24a-Clos(51-526, Δ [182-190], R181Q) and pET24a-T7tag-Clos (51-526) were induced and harvested 4 hr after induction. Cells were lysed and the inclusion bodies, isolated by centrifugation, were boiled in SDS sample buffer. Lane 1: clostripain (51-526, Δ [182-190], R181Q) expressed in BL21 (DE3)pLysS. Lane 2: clostripain (51-526, Δ [182-190], R181Q) expressed in BL21(DE3). Lane 3: T7tag-clostripain (51-526) expressed in BL21(DE3). Lane M: molecular weight markers, as indicated (kDa). The gel was stained with Coomassie blue. The bold arrow indicates the position of clostripain (51-526, Δ [182-190], R181Q).
Figure 8:
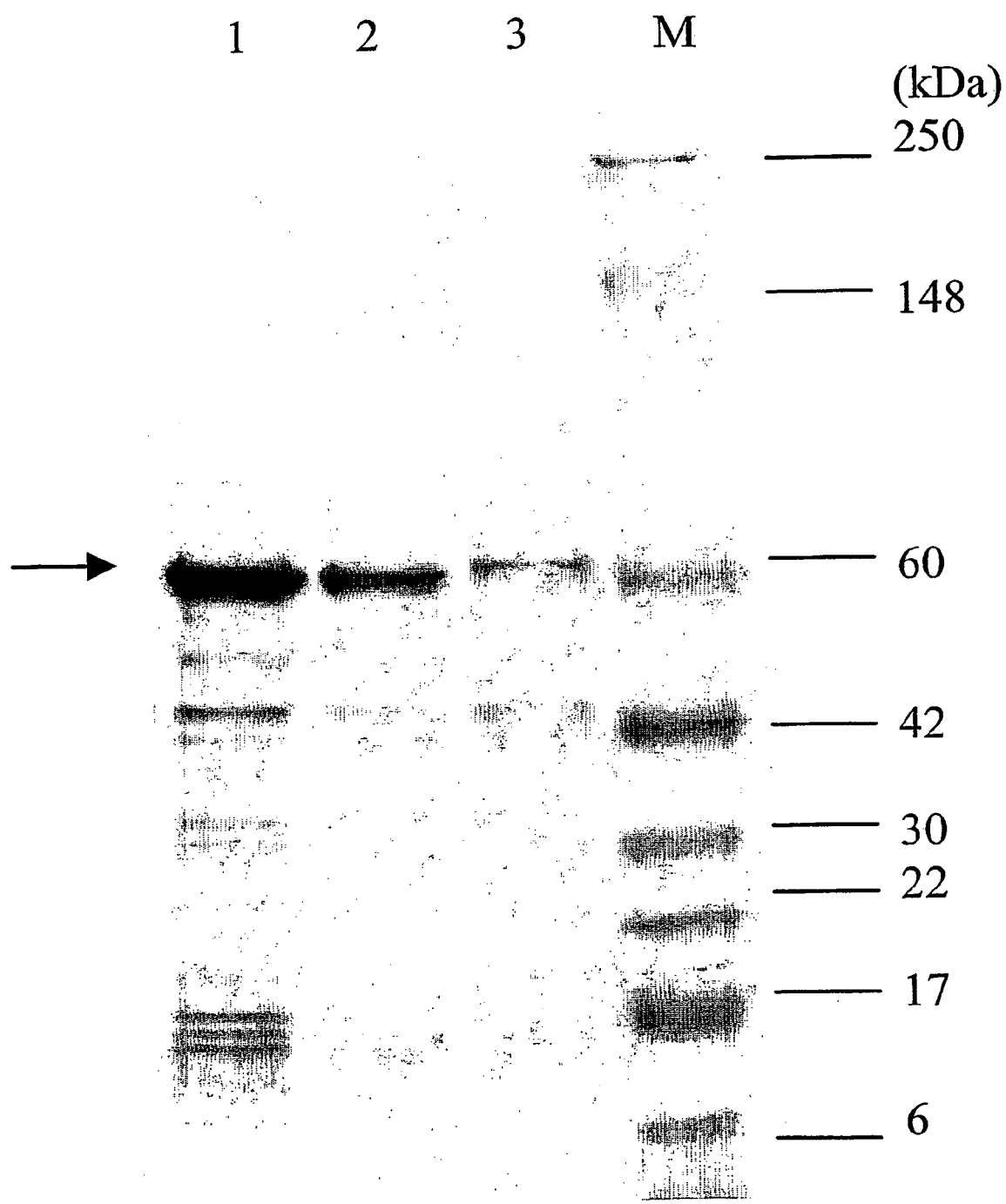

Clostripain is expressed naturally in the anaerobic bacteria *Clostridium histoliticum*. Clostripain selectively hydrolyzes the carboxyl peptide linkage of positively charged amino acids. The preferred cleavage site in a polypeptide is on the carboxyl-side of an arginine residue and, under selective conditions, peptide bond cleavage can be so limited.

Native clostripain is a heterodimeric protein of 467 amino acids; the molecular weight of the heavy and light chains are approximately 43,000 and 15,000 Daltons respectively. The clostripain precursor protein comprises a putative signal peptide (27aa), propeptide (23aa), light chain subunit (131aa), linker peptide (9 aa), and heavy chain subunit (336aa).

Previous attempts to purify clostripain from culture filtrates of *Clostridium histoliticum* by conventional methods and through use of recombinant expression in *E. coli* have produced small quantities of clostripain having low activity. These failings of the past have been overcome by the surprising discovery of DNA constructs and methods that can be used to express large quantities of high activity clostripain that are put forth herein. Accordingly, the present invention relates to nucleic acid expression constructs that can be used to express large quantities of high activity clostripain in prokaryotic and eukaryotic cells.

I. Expression Cassette

The invention provides expression cassettes capable of directing the expression of clostripain. An expression cassette of the invention preferably expresses an mRNA having a translation initiation sequence operably linked to an open reading frame that encodes clostripain. A preferred translation initiation sequence is the T7 tag sequence as described herein (SEQ ID NO: 17 and 18). The invention also provides an expression cassette capable of directing the expression of a polypeptide having clostripain operably linked to an inclusion body fusion partner. The invention also provides an expression cassette capable of directing the expression clostripain operably linked to an inclusion body fusion partner and a cleavable linker peptide.

Promoters

The expression cassette of the invention includes a promoter. Any promoter able to direct transcription of the expression cassette may be used. Accordingly, many promoters may be included within the expression cassette of the invention. Some useful promoters include, constitutive promoters, inducible promoters, regulated promoters, cell specific promoters, viral promoters, and synthetic promoters. A promoter is a nucleotide sequence which controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

Examples of Promoters Suitable for Use in Bacterial Cells

For expression of clostripain or a variant of clostripain in a bacterium, an expression cassette having a bacterial promoter may be used. A bacterial promoter is any DNA sequence capable of binding bacterial RNA polymerase and initiating the downstream (3") transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18:173 (1984)). Regulated expression may therefore be positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (Chang et al., *Nature*, 198:1056 (1977)), and maltose. Additional examples include promoter sequences derived from biosynthetic enzymes such as tryptophan (trp) (Goeddel et al., *N.A.R* 8: 4057 (1980); Yelverton et al., *N.A.R*, 9: 731 (1981); U.S. Pat. No. 4,738,921; and EPO Publ. Nos. 036 776 and 121 775). The β-lactamase (bla) promoter system (Weissmann, "The cloning of interferon and other mistakes", in: Interferon 3 (ed. I. Gresser), 1981), and bacteriophage lambda $P_L$ (Shimatake et al., *Nature*, 292:128 (1981)) and T5 (U.S. Pat. No. 4,689, 406) promoter systems also provide useful promoter sequences. A preferred promoter is the Chlorella Virus promoter. (U.S. Pat. No. 6,316,224).

Synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both trp promoter and lac operon sequences that is regulated by the lac repressor (Amann et al., *Gene*, 25:167 (1983); de Boer et al., *Proc. Natl. Acad. Sci. USA*, 80: 21 (1983)). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.*, 189: 113 (1986); Tabor et al., *Proc. Natl. Acad. Sci. USA* 82:1074 (1985)). In addition, a hybrid promoter can also be comprised of a bacteriophage promoter and an *E. coli* operator region (EPO Publ. No. 267 851).

Examples of Promoters Suitable for Use in Insect Cells

An expression cassette having a baculovirus promoter can be used for expression of clostripain or a variant of clostripain in an insect cell. A baculovirus promoter is any DNA sequence capable of binding a baculovirus RNA polymerase and initiating transcription of a coding sequence into mRNA. A promoter will have a transcription initiation region which is usually placed proximal to the 5' end of the coding sequence. This transcription initiation region usually includes an RNA polymerase binding site and a transcription initiation site. A second domain called an enhancer may be present and is usually distal to the structural gene. A baculovirus promoter may be a regulated promoter or a constitutive promoter. Useful promoter sequences may be obtained from structural genes that are transcribed at times late in a viral infection cycle. Examples include sequences derived from the gene encoding the baculoviral polyhedron protein (Friesen et al., "The Regulation of Baculovirus Gene, Expression", in: The Molecular Biology of Baculoviruses (ed. Walter Doerfler), 1986; and EPO Publ. Nos. 127 839 and 155 476) and the gene encoding the baculoviral p10 protein (Vlak et al., *J. Gen. Virol.*, 69: 765 (1988)).

Examples of Promoters Suitable for Use in Yeast Cells

Promoters that are functional in yeast are known to those of ordinary skill in the art. In addition to an RNA polymerase binding site and a transcription initiation site, a yeast promoter may also have a second region called an upstream activator sequence. The upstream activator sequence permits regulated expression that may be induced. Constitutive expression occurs in the absence of an upstream activator sequence. Regulated expression may be either positive or negative, thereby either enhancing or reducing transcription.

Promoters for use in yeast may be obtained from yeast genes that encode enzymes active in metabolic pathways. Examples of such genes include alcohol dehydrogenase (ADH) (EPO Publ. No. 284 044), enolase, glucokinase, glucose -6-phosphate isomerase, glyceraldehyde-3-phosphatedehydrogenase (GAP or GAPDH), hexokinase, phosphofructokinase, 3-phosphoglyceratemutase, and pyruvate kinase (PyK). (EPO Publ. No. 329 203). The yeast PHO5 gene, encoding acid phosphatase, also provides useful promoter sequences. (Myanohara et al., *Proc. Natl. Acad. Sci. USA*, 80: 1 (1983)).

Synthetic promoters which do not occur in nature may also be used for expression of clostripain or a variant of clostripain in yeast. For example, upstream activator sequences from one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of nonyeast origin that have the ability to bind yeast RNA polymerase and initiate transcription. Examples of such promoters are known in the art. (Cohen et al., *Proc. Natl. Acad. Sci. USA* 77: 1078 (1980); Henikoff et al., *Nature*, 283:835 (1981); Hollenberg et al., *Curr. Topics Microbiol. Immunol.*, 96: 119 (1981); Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Puhler), 1979; Mercerau-Puigalon et al., *Gene*, 11:163 (1980); Panthier et al., *Curr. Genet.*, 2:109 (1980)).

Examples of Promoters Suitable for Use in Mammalian Cells

Many mammalian promoters are known in the art that may be used in conjunction with the expression cassette of the invention. Mammalian promoters often have a transcription initiating region, which is usually placed proximal to the 5' end of the coding sequence, and a TATA box, usually located 25-30 base pairs (bp) upstream of the transcription initiation site. The TATA box is thought to direct RNA polymerase It to begin RNA synthesis at the correct site. A mammalian promoter may also contain an upstream promoter element, usually located within 100 to 200 bp upstream of the TATA box. An upstream promoter element determines the rate at which transcription is initiated and can act in either orientation (Sambrook et al., "Expression of Cloned Genes in Mammalian Cells", in: Molecular Cloning: A Laboratory Manual, 2nd ed., 1989).

Mammalian viral genes are often highly expressed and have a broad host range; therefore sequences encoding mammalian viral genes often provide useful promoter sequences. Examples include the SV40 early promoter, mouse mammary tumour virus LTR promoter, adenovirus major late promoter (Ad MLP), and herpes simplex virus promoter. In addition, sequences derived from non-viral genes, such as the murine metallothioneih gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. (Maniatis et al., *Science*, 236:1237 (1987); Alberts et al., Molecular Biology of the Cell, 2nd ed., 1989)). Enhancer elements derived from viruses are often times useful, because they usually have a broad host range. Examples include the SV40 early gene enhancer (Dijkema et al., *EMBO J.*, 4:761 (1985)) and the enhancer/promoters derived from the long terminal repeat (LTR) of the Rous Sarcoma Virus (Gorman et al., *Proc. Natl. Acad. Sci. USA*, 79:6777 (1982b)) and from human cytomegalovirus (Boshart et al., *Cell*, 41: 521 (1985)). Additionally, some enhancers are regulatable and become active only in the presence of an inducer, such as a hormone or metal ion (Sassone-Corsi and Borelli, *Trends Genet.*, 2:215 (1986); Maniatis et al., *Science*, 236:1237 (1987)).

It is understood that many promoters and associated regulatory elements may be used within the expression cassette of the invention to transcribe an encoded clostripain or variant of clostripain. The promoters described above are provided merely as examples and are not to be considered as a complete list of promoters that are included within the scope of the invention.

Translation Initiation Sequence

The expression cassette of the invention may contain a nucleic acid sequence for increasing the translation efficiency of an mRNA encoding clostripain or a variant thereof according to the invention. Such increased translation serves to increase production of clostripain. The presence of an efficient ribosome binding site is useful for gene expression in prokaryotes. In bacterial mRNA a conserved stretch of six nucleotides, the Shine-Dalgarno sequence, is usually found upstream of the initiating AUG codon. (Shine et al., *Nature,* 254: 34 (1975)). This sequence is thought to promote ribosome binding to the mRNA by base pairing between the ribosome binding site and the 3' end of *Escherichia coli* 16S rRNA. (Steitz et al., "Genetic signals and nucleotide sequences in messenger RNA", in: Biological Regulation and Development: Gene Expression (ed. R. F. Goldberger), 1979)). Such a ribosome binding site, or operable derivatives thereof, are included within the expression cassette of the invention.

A translation initiation sequence can be derived from any expresssed *Escherichia coli* gene and can be used within an expression cassette of the invention. Preferably the gene is a highly expressed gene. A translation initiation sequence can be obtained via standard recombinant methods, synthetic techniques, purification techniques, or combinations thereof, which are all well known. (Ausubel et al., *Current Protocols in Molecular Biology*, Green Publishing Associates and Wiley Interscience, NY. (1989); Beaucage and Caruthers, *Tetra. Letts.,* 22:1859 (1981); VanDevanter et al., *Nucleic Acids Res.,* 12:6159 (1984)). Alternatively, translational start sequences can be obtained from numerous commercial vendors. (Operon Technologies; Life Technologies Inc, Gaithersburg, Md.). In a preferred embodiment, the T7tag sequence (SEQ ID NO: 17 and 18) is used. The T7tag sequence is derived from the highly expressed T7 Gene 10 cistron. Other examples of translation initiation sequences include, but are not limited to, the maltose-binding protein (Mal E gene) start sequence (Guan et al., *Gene,* 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Trp E gene (Ausubel et al., 1989*, Current Protocols in Molecular Biology*, Chapter 16, Green Publishing Associates and Wiley Interscience, NY).

Eucaryotic mRNA does not contain: a Shine-Dalgarno sequence. Instead, the selection of the translational start codon is usually determined by its proximity to the cap at the 5' end of an mRNA. The nucleotides immediately surrounding the start codon in eucaryotic mRNA influence the efficiency of translation. Accordingly, one skilled in the art can determine what nucleic acid sequences will increase translation of clostripain or a variant thereof that is encoded by an expression cassette of the invention. Such nucleic acid sequences are within the scope of the invention.

Inclusion Bode Fusion Partner

The expression cassette of the present invention encodes an inclusion body fusion partner that may be operably linked to clostripain or a variant of clostripain. It has been surprisingly found that the amino acid sequence of an inclusion body fusion partner can be altered to produce inclusion bodies that exhibit useful characteristics. These useful characteristics may provide isolation enhancement to inclusion bodies that are formed from clostripain or a variant of clostripain that is operably linked to an inclusion body fusion partner of the invention. Isolation enhancement may allow clostripain or a variant of clostripain that is linked to an inclusion body fusion partner to be isolated and purified more readily than the clostripain or variant thereof in the absence of the inclusion body fusion partner. For example, the inclusion body fusion partner may be altered to produce inclusion bodies that are more or less soluble under a certain set of conditions. Those of skill in the art realize that solubility is, dependent on a number of variables that include, but are not limited to, pH, temperature, salt concentration, and protein concentration. Thus, an inclusion body fusion partner of the invention may be altered to produce an inclusion body having desired solubility under differing conditions.

In another example, an inclusion body fusion partner of the invention may be altered to produce inclusion bodies containing clostripain that have greater or lesser self-association. Self-association refers to the strength of the interaction between two or more clostripain molecules that are linked to an inclusion body fusion partner and that form an inclusion body. Such self-association may be determined though use of a variety of known methods used to measure protein-protein interactions. Such methods are known in the art and have been described. Freifelder, Physical Biochemistry: Applications to Biochemistry and Molecular Biology, W.H. Freeman and Co., 2nd edition, New York, N.Y. (1982). Self-adhesion can be used to produce inclusion bodies that exhibit varying stability to purification. For example, greater self-adhesion may be desirable to stabilize inclusion bodies against dissociation in instances where harsh conditions are used to isolate the inclusion bodies from a cell. Such conditions may be encountered if inclusion bodies are being isolated from cells having thick cell walls. However, where mild conditions are used to isolate the inclusion bodies, less self-adhesion may be desirable as it may allow the linked clostripain composing the inclusion body to be more readily solubilized or processed. Accordingly, an inclusion body fusion partner of the invention may be altered to provide a desired level of self-adhesion for a given set of conditions.

Such an inclusion body fusion partner may be linked to the amino-terminus, the carboxyl-terminus, or both termini of clostripain to cause the formation of an inclusion body. An inclusion body fusion partner is of an adequate size to cause the operably linked clostripain to form an inclusion body. It is preferred that the inclusion body fusion partner is 100 or less amino acids, more preferably 50 or less amino acids, and most preferably 31 or less amino acids in length. For example, the inclusion body fusion partner can have an amino acid sequence corresponding to any one of SEQ ID Nos: 1-16. These amino acid sequences have been surprisingly found to cause linked polypeptides to form inclusion bodies. Furthermore the sequence of these inclusion body fusion partners may be altered to provide isolation enhancement to linked a clostripain. An inclusion body fusion partner can also have an amino acid sequence that is a variant of any one of SEQ ID NOs: 1-16 and which causes inclusion body formation by an operably linked clostripain molecule. An inclusion body fusion partner can also have an amino acid sequence corresponding to any one of SEQ ID NOs: 1-16, or a variant thereof, in addition to other amino acids which cause inclusion body formation by an operably linked clostripain molecule. An example of prefered additional amino acids to which the inclusion body fusion partner can be linked is the T7tag sequence (SEQ ID NO: 17 and 18).

Termination Sequences

Examples of Termination Sequences Suitable for Use in Bacteria

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Examples of Termination Sequences Suitable for Use in Mammalian Cells

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation (Birnstiel et al., *Cell,* 41:349 (1985); Proudfoot and Whitelaw, "Termination and 3' end processing of eukaryotic RNA", in: Transcription and Splicing (eds. B. D. Hames and D. M. Glover) 1988, Proudfoot, *Trends Biochem. Sci.,* 14:105 (1989)). These sequences direct the transcription of an mRNA which can be translated into the polypeptide encoded by the DNA Examples of transcription terminator/polyadenylation signals include those derived from SV40 (Sambrook et al., "Expression of cloned genes in cultured mammalian cells", in: Molecular Cloning: A Laboratory Manual, 1989).

Examples of Termination Sequences Suitable for Use in Yeast and Insect Cells

Transcription termination sequences recognized by yeast are regulatory regions that are usually located 3' to the translation stop codon. Examples of transcription terminator sequences that may be used as termination sequences in yeast and insect expression systems are well known. (Lopez-Ferber et al., *Methods Mol. Biol.,* 39:25 (1995); King and Possee, The baculovirus expression system. A laboratory guide. Chapman and Hall, London, England (1992); Gregor and Proudfoot, *EMBO J.,* 17:4771 (1998); O'Reilly et al., Baculovirus expression vectors: a laboratory manual. W.H. Freeman & Company, New York, N.Y. (1992); Richardson, *Crit. Rev. Biochem. Mol. Biol.,* 28:1 (1993), Zhao et al., *Microbiol. Mol. Biol. Rev.,* 63:405 (1999)).

II. Nucleic Acid Constructs and Expression Cassettes

Nucleic acid constructs and expression cassettes can be created through use of recombinant methods that are well known. (Sambrook and Russell, Molecular Cloning: A Laboratory Manual, 3rd edition (Jan. 15, 2001) Cold Spring Harbor Laboratory Press, ISBN: 0879695765; Ausubel et al., *Current Protocols in Molecular Biology*, Green Publishing Associates and Wiley Interscience, NY (1989)). Generally, recombinant methods involve preparation of a desired DNA fragment and ligation of that DNA fragment into a preselected position in another DNA vector, such as a plasmid.

In a typical example, a desired DNA fragment is first obtained by digesting a DNA that contains the desired DNA fragment with one or more restriction enzymes that cut on both sides of the desired DNA fragment. The restriction enzymes may leave a "blunt" end or a "sticky" end. A "blunt" end means that the end of a DNA fragment does not contain a region of single-stranded DNA. A DNA fragment having a "sticky" end means that the end of the DNA fragment has a region of single-stranded DNA. The sticky end may have a 5' or a 3' overhang. Numerous restriction enzymes are commercially available and conditions for their use are also well known. (USB, Cleveland, Ohio; New England Biolabs, Beverly, Mass.). The digested DNA fragments may be extracted according to known methods, such as phenol/chloroform extraction, to produce DNA fragments free from restriction enzymes. The restriction enzymes may also be inactivated with heat or other suitable means. Alternatively, a desired DNA fragment may be isolated away from additional nucleic acid sequences and restriction enzymes through use of electrophoresis, such as agarose gel or polyacrylamide gel electrophoresis. Generally, agarose gel electrophoresis is used to isolate large nucleic acid fragments while polyacrylamide gel electrophoresis is used to isolate small nucleic acid fragments. Such methods are used routinely to isolate DNA fragments. The electrophoresed DNA fragment can then be extracted from the gel following electrophoresis through use of many known methods, such as electoelution, column chromatography, or binding to glass-beads. Many kits containing materials and methods for extraction and isolation of DNA fragments are commercially available. (Qiagen, Venlo, Netherlands; Qbiogene, Carlsbad, Calif.).

The DNA segment into which the fragment is going to be inserted is then digested with one or more restriction enzymes. Preferably, the DNA segment is digested with the same restriction enzymes used to produce the desired DNA fragment. This will allow for directional insertion of the DNA fragment into the DNA segment based on the orientation of the complimentary ends. For example, if a DNA fragment is produced that has an EcoRI site on its 5' end and a BamHI site at the 3' end, it may be directionally inserted into a DNA segment that has been digested with EcoRI and BamHI based on the complementarity of the ends of the respective DNAs. Alternatively, blunt ended cloning may be used if no convenient restriction sites exist that allow for directional cloning. For example, the restriction enzyme BsaAI leaves DNA ends that do not have a 5' or 3' overhang. Blunt ended cloning may be used to insert a DNA fragment into a DNA segment that was also digested with an enzyme that produces a blunt end. Additionally, DNA fragments and segments may be digested with a restriction enzyme that produces an overhang and then treated with an appropriate enzyme to produce a blunt end. Such enzymes include polymerases and exonucleases. Those of skill in the art know how to use such methods alone or in combination to selectively produce DNA fragments and segments that may be selectively combined.

A DNA fragment and a DNA segment can be combined though conducting a ligation reaction. Ligation links two pieces of DNA through formation of a phosphodiester bond between the two pieces of DNA. Generally, ligation of two or more pieces of DNA occurs through the action of the enzyme ligase when the pieces of DNA are incubated with ligase under appropriate conditions. Ligase and methods and conditions for its use are well known in the art and are commercially available.

The ligation reaction or a portion thereof is then used to transform cells to amplify the recombinant DNA formed, such as a plasmid having an insert. Methods for introducing DNA into cells are well known and are disclosed herein.

Those of skill in the art recognize that many techniques for producing recombinant nucleic acids can be used to produce an expression cassette or nucleic acid construct of the invention. These techniques may be used to isolate individual components of an expression cassette of the invention from existing DNA constructs and insert the components into another piece of DNA to construct an expression cassette. Such techniques can also be used to isolate an expression cassette of the invention and insert it into a desired vector to create a nucleic acid construct of the invention. Additionally, open reading frames may be obtained from genes that are available or are obtained from nature. Methods to isolate and clone genes from nature are known. For example, a desired open reading frame may be obtained through creation of a cDNA library from cells that express a desired polypeptide. The open reading frame may then be inserted into an expression cassette of the invention to allow for production of an encoded clostripain.

Vectors

Vectors that may be used include, but are not limited to, those able to be replicated in prokaryotes and eukaryotes. For example, vectors may be used that are replicated in bacteria, yeast, insect cells, and mammalian cells. Vectors may be exemplified by plasmids, phagemids, bacteriophages, viruses, cosmids, and F-factors. The invention includes any vector into which the expression cassette of the invention may be inserted and replicated in vitro or in vivo. Specific vectors may be used for specific cells types. Additionally, shuttle vectors may be used for cloning and replication in more than one cell type. Such shuttle vectors are known in the art. The nucleic acid constructs may be carried extrachromosomally within a host cell or may be integrated into a host cell chromosome. Numerous examples of vectors are known in the art and are commercially available. (Sambrook and Russell, Molecular Cloning: A Laboratory Manual, 3rd edition (Jan. 15, 2001) Cold Spring Harbor Laboratory Press, ISBN: 0879695765; New England Biolab, Beverly, Mass.; Stratagene, La Jolla, Calif.; Promega, Madison, Wis.; ATCC, Rockville, Md.; CLONTECH, Palo Alto, Calif.; Invitrogen, Carlabad, Calif.; Origene, Rockville, Md.; Sigma, St. Louis, Mo.; Pharmacia, Peapack, N.J.; USB, Cleveland, Ohio). These vectors also provide many promoters and other regulatory elements that those of skill in the art may include within the nucleic acid constructs of the invention through use of known recombinant techniques.

Examples of Vectors Suitable for Use in Prokayrotes

A nucleic acid construct for use in a prokaryote host, such as a bacteria, will preferably include a replication system allowing it to be maintained in the host for expression or for cloning and amplification. In addition, a nucleic acid construct may be present in the cell in either high or low copy number. Generally, about 5 to about 200, and usually about 10 to about 150 copies of a high copy number nucleic acid construct will be present within a host cell. A host containing a high copy number plasmid will preferably contain at least about 10, and more preferably at least about 20 plasmids. Generally, about 1 to 10, and usually about 1 to 4 copies of a low copy number nucleic acid construct will be present in a host cell. The copy number of a nucleic acid construct may be controlled by selection of different origins of replication according to methods known in the art. Sambrook and Russell, Molecular Cloning: A Laboratory Manual, 3rd edition (Jan. 15, 2001) Cold Spring Harbor Laboratory Press, ISBN: 0879695765.

A nucleic acid construct containing an expression cassette can be integrated into the genome of a bacterial host cell through use of an integrating vector. Integrating vectors usually contain at least one sequence that is homologous to the bacterial chromosome which allows the vector to integrate. Integrations are thought to result from recombinations between homologous DNA in the vector and the bacterial chromosome. For example, integrating vectors constructed with DNA from various *Bacillus* strains integrate into the Bacillus chromosome (PO Publ. No. 127 328). Integrating vectors may also contain bacteriophage or transposon sequences.

Extrachromosomal and integrating nucleic acid constructs may contain selectable markers to allow for the selection of bacterial strains that have been transformed. Selectable markers can be expressed in the bacterial host and may include genes which render bacteria resistant to drugs such as ampicillin, chloramphenicol erythromycin, kanamycin (neomycin), and tetracycline (Davies et al., *Ann. Rev. Microbiol.*, 32: 469 (1978)). Selectable markers may also include biosynthetic genes, such as those in the histidine, tryptophan, and leucine biosynthetic pathways.

Numerous vectors, either extra-chromosomal or integrating vectors, have been developed for transformation into many bacteria. For example, vectors have been developed for the following bacteria: *B. subtilis* (Palva et al., *Proc. Natl. Acad. Sci. USA*, 79: 5582 (1982); EPO Publ. Nos. 036 259 and 063 953; PCT Publ. No. WO 84/04541), *E. coli* (Shimatake et al., *Nature*, 292:128 (1981); Amann et al., *Gene*, 40:183 (1985); Studier et al., *J. Mol. Biol.*, 189:113 (1986); EPO Publ. Nos. 036 776, 136 829 and 136 907)), *Streptococcus cremoris* (Powell et al., *Appl. Environ. Microbiol.*, 54: 655 (1988)); *Streptococcus lividans* (Powell et al., *Appl. Environ. Microbiol.*, 54:655 (1988)), and *Streptomyces lividans* (U.S. Pat. No. 4,745,056). Numerous vectors are also commercially available (New England Biolabs, Beverly, Mass.; Stratagene, La Jolla, Calif.).

Examples of Vectors Suitable for Use in Yeast

Many vectors may be used to construct a nucleic acid construct that contains an expression cassette of the invention and that provides for the expression of clostripain in yeast. Such vectors include, but are not limited to, plasmids and yeast artificial chromosomes. Preferably the vector has two replication systems, thus allowing it to be maintained, for example, in yeast for expression and in a prokaryotic host for cloning and amplification. Examples of such yeast-bacteria shuttle vectors include YEp24 (Botstein, et al., *Gene*, 8:17 (1979)), pC1/1 (Brake et al., *Proc. Natl. Acad. Sci. USA*, 81:4642 (1984)), and YRp17 (Stinchcomb et al., *J. Mol. Biol.*, 158:157 (1982)). A vector may be maintained within a host cell in either high or low copy number. For example, a high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the encoded clostripain or variant of clostripain on the host. (Brake et al., *Proc. Natl. Acad. Sci. USA*, 81:4642 (1984)).

A nucleic acid construct may also be integrated into the yeast genome with an integrating vector. Integrating vectors usually contain at least one sequence homologous to a yeast chromosome that allows the vector to integrate, and preferably contain two homologous sequences flanking an expression cassette of the invention. Integrations appear to result from recombinations between homologous DNA in the vector and the yeast chromosome. (Orr-Weaver et al., *Methods in Enzymol.*, 101:228 (1983)). An integrating vector may be directed to a specific locus in yeast by selecting the appropriate homologous sequence for inclusion in the vector. One or more nucleic acid constructs may integrate, which may affect the level of recombinant protein produced. (Rine et al., *Proc. Natl. Acad. Sci. USA*, 80:6750 (1983)). The chromosomal sequences included in the vector can occur either as a single segment in the vector, which results in the integration of the entire vector, or two segments homologous to adjacent segments in the chromosome and flanking an expression cassette included in the vector, which can result in the stable integration of only the expression cassette.

Extrachromosomal and integrating nucleic acid constructs may contain selectable markers that allow for selection of yeast, strains that have been transformed. Selectable markers may include, but are not limited to, biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a selectable marker may also provide yeast with the ability to grow in the presence of toxic compounds, such as metal. For example, the presence of CUP1 allows yeast to grow in the presence of copper ions. (Butt et al., *Microbiol. Rev.*, 51:351 (1987)).

Many vectors have been developed for transformation into many yeasts. For example, vectors have been developed for the following yeasts: *Candida albicans* (Kurtz et al., *Mol. Cell. Biol.*, 6:142 (1986)), *Candida maltose* (Kunze et al., *J. Basic Microbiol.*, 25:141 (1985)), *Hansenula polymorpha* (Gleeson et al., *J. Gen. Microbiol.*, 132:3459 (1986); Roggenkamp et al., *Mol. Gen. Genet.* 202:302 (1986), *kluyveromyces fragilis* (Das et al., *J. Bacteriol.*, 158: 1165 (1984)), *Kluyveromyces lactis* (De Louvencourt et al., *J. Bacteriol.*, 154:737 (1983); van den Berg et al., *Bio/Technology*, 8:135 (1990)), *Pichia guillerimondii* (Kunze et al., *J. Basic Microbiol.*, 25:141 (1985)), *Pichia pastoris* (Cregg et al., *Mol. Cell. Biol.*, 5: 3376, 1985; U.S. Pat. Nos. 4,837,148 and 4,929,555), *Saccharomyces cerevisiae* (Hinnen et al., *Proc. Natl. Acad. Sci. USA* 75:1929 (1978); Ito et al., *J. Bacteriol.*, 153:163 (1983)), *Schizosaccharomyces pombe* (Beach and Nurse, *Nature*, 300:706 (1981)), and *Yarrowia lipolytica* (Davidow et al., *Curr. Genet.*, 10:39 (1985); Gaillardin et al., *Curr. Genet.*, 10:49 (1985)).

Examples of Vectors Suitable for Use in Insect Cells

Baculovirus vectors have been developed for infection into several insect cells and may be used to produce nucleic acid constructs that contain an expression cassette of the invention. For example, recombinant baculoviruses have been developed for *Aedes aegypti*, *Autographa californica*, *Bombyx mori*, *Drosophila melanogaster*, *Spodoptera frugiperda*, and *Trichoplusia ni* (PCT Pub. No. WO 89/046699; Carbonell et al., *J. Virol.*, 56:153 (1985); Wright, *Nature*, 321: 718 (1986); Smith et al., *Mol. Cell. Biol.*, 3: 2156 (1983); and see generally, Fraser et al., *In Vitro Cell. Dev. Biol.*, 25:225 (1989)). Such a baculovirus vector may be used to introduce an expression cassette into an insect and provide for the expression of clostripain or a variant of clostripain within the insect cell.

Methods to form a nucleic acid construct having an expression cassette of the invention inserted into a baculovirus vector are well known in the art. Briefly, an expression cassette of the invention is inserted into a transfer vector, usually a bacterial plasmid which contains a fragment of the baculovirus genome, through use of common recombinant methods. The plasmid may also contain a polyhedrin polyadenylation signal (Miller et al., *Ann. Rev. Microbiol.* 42:177 (1988)) and a prokaryotic selection marker, such as ampicillin resistance, and an origin of replication for selection and propagation in *Escherichia coli*. A convenient transfer vector for introducing foreign genes into AcNPV is pAc373. Many other vectors, known to those of skill in the art, have been designed. Such a vector is pVL985 (Luckow and Summers, *Virology*, 17:31 (1989)).

A wild-type baculoviral genome and the transfer vector having an expression cassette insert are transfected into an insect host cell where the vector and the wild-type viral genome recombine. Methods for introducing an expression cassette into a desired site in a baculovirus virus are known in the art. (Summers and Smith, Texas Agricultural Experiment Station Bulletin No. 1555, 1987. Smith et al., *Mol. Cell. Biol.*, 3:2156 (1983); and Luckow and Summers, *Virology*, 17:31 (1989)). For example, the insertion can be into a gene such as the polyhedrin gene, by homologous double crossover recombination; insertion can also be into a restriction enzyme site engineered into the desired baculovirus gene (Miller et al., *Bioessays*, 4:91 (1989)). The expression cassette, when cloned in place of the polyhedrin gene in the nucleic acid construct, will be flanked both 5' and 3' by polyhedrin-specific sequences. An advantage of inserting an expression cassette into the polyhedrin gene is that occlusion bodies resulting from expression of the wild-type polyhedrin gene may be eliminated. This may decrease contamination of clostripain or variants thereof that are produced through expression and formation of occlusion bodies in insect cells by wild-type proteins that would otherwise form occlusion bodies in an insect cell having a functional copy of the polyhedrin gene.

The packaged recombinant virus is expressed and recombinant plaques are identified and purified. Materials and methods for baculovirus and insect cell expression systems are commercially available in kit form. (Invitrogen, San Diego, Calif., USA ("MaxBac" kit)). These techniques are generally known to those skilled in the art and fully described in Summers and Smith, Texas Agricultural Experiment Station Bulletin No. 1555, 1987.

Plasmid-based expression systems have also been developed the may be used to introduce an expression cassette of the invention into an insect cell and produce clostripain or a variant of clostripain. (McCarroll and, King, *Curr. Opin. Biotechnol.*, 8:590 (1997)). These plasmids offer an alternative to the production of a recombinant virus for the production of clostripain.

Examples of Vectors Suitable for Use in Mammalian Cells

An expression cassette of the invention may be inserted into many mammalian vectors that are known in the art and are commercially available. (CLONTECH, Carlsbad, Calif.; Promega, Madision, Wis.; Invitrogen, Carlsbad, Calif.). Such vectors may contain additional elements such as enhancers and introns having functional splice donor and acceptor sites. Nucleic acid constructs may be maintained extrachromosomally or may integrate in the chromosomal DNA of a host cell. Mammalian vectors include those derived from animal viruses, which require trans-acting factors to replicate. For example, vectors containing the replication systems of papovaviruses, such as SV40 (Gluzman, *Cell*, 23:175 (1981)) or polyomaviruses, replicate to extremely high copy number in the presence of the appropriate viral T antigen. Additional examples of mammalian vectors include those derived from bovine papillomavirus and Epstein-Barr virus. Additionally, the vector may have two replication systems, thus allowing it to be maintained, for example, in mammalian cells for expression and in a prokaryotic host for cloning and amplification. Examples of such mammalian-bacteria shuttle vectors include pMT2 (Kaufman et al., *Mol. Cell. Biol.*, 9:946 (1989)) and pHEBO (Shimizu et al., *Mol. Cell. Biol.*, 6:1074 (1986)).

III. Cells Containing an Expression Cassette or a Nucleic Acid Construct

The invention provides cells that contain an expression cassette of the invention or a nucleic acid construct of the invention. Such cells may be used for expression of clostripain or a variant of clostripain. Such cells may also be used for the amplification of nucleic acid constructs. Many cells are suitable for amplifying nucleic acid constructs and for expressing clostripain. These cells may be prokaryotic or eukaryotic cells.

In a preferred embodiment, bacteria are used as host cells. Examples of bacteria include, but are not limited to, Gram-negative and Gram-positive organisms. *Escherichia coli* is a preferred organism for expression of clostripain and variants of clostripain. *Escherichia coli* is also preferred for amplification of nucleic acid constructs of the invention. Many publicly available *E. coli* strains include K-strains such as MM294 (ATCC 31, 466); X1776 (ATCC 31, 537); KS 772 (ATCC 53, 635); JM109; MC1061; HMS174; and the B-strain BL21. Recombination minus strains may be used for nucleic acid construct amplification to avoid recombination events. Such recombination events may remove concatamers of open reading frames as well as cause inactivation of an expression cassette. Furthermore, bacterial strains that do not express a select protease may also be useful for expression of clostripain or variants thereof to reduce proteolysis of the expressed polypeptides. Such a strain is exemplified by Y1090hsdR which is deficient in the lon protease.

Eukaryotic cells may also be used to produce clostripain or variants thereof as well as for amplifying nucleic acid constructs. Examples of eukaryotic cell lines that may be used include, but are not limited to: AS52, H187, mouse L cells, NIH-3T3, HeLa, Jurkat, CHO-K1, COS-7, BHK-21, A -431, HEK293, L6, CV-1, HepG2, HC11, MDCK, silkworm cells, mosquito cells, and yeast.

Methods for introducing exogenous DNA into bacteria are well known in the art, and usually include either the transformation of bacteria treated with $CaCl_2$ or other agents, such as divalent cations and DMSO. DNA can also be introduced into bacterial cells by electroporation, use of a bacteriophage, or ballistic transformation. Transformation procedures usually vary with the bacterial species to be transformed (Masson et al., *FEMS Microbiol. Lett.*, 60:273 (1989); Palva et al., *Proc. Natl. Acad. Sci. USA*, 79:5582 (1982); EPO Publ. Nos. 036 259 and 063 953; PCT Publ. No. WO 84/04541 *[Bacillus]*, Miller et al., *Proc. Natl. Acad. Sci. USA*, 8:856 (1988); Wang et al., *J. Bacteriol.*, 172:949 (1990) *[Campylobacter]*, Cohen et al., *Proc. Natl. Acad. Sci. USA*, 69:2110 (1973); Dower et al., *Nuc. Acids Res.*, 16:6127 (1988); Kushner, "An improved method for transformation of *Escherichia coli* with ColE1-derived plasmids", in: Genetic Engineering: Proceedings of the International Symposium on Genetic Engineering (eds. H. W. Boyer and S. Nicosia), 1978; Mandel et al., *J. Mol. Biol.*, 53:159 (1970); Taketo, *Biochim. Biophys. Acta*, 949: 318 (1988) *[Escherichia]*, Chassy et al., *FEMS Microbiol. Lett.*, 44:173 (1987) *[Lactobacillus]*, Fiedler et al., *Anal. Biochem*, 170:38 (1988) *[Pseudomonas]*, Augustin et al., *FEMS Microbiol. Lett.*, 66:203 (1990) *[Staphylococcus]*, Barany et al., *J. Bacteriol.*, 144:698 (1980); Harlander, "Transformation of *Streptococcus lactis* by electroporation", in: Streptococcal Genetics (ed. J. Ferretti and R. Curtiss E), 1987; Perry et al., *Infec. Immun.*, 32:1295 (1981); Powell et al., *Appl. Environ. Microbiol.*, 54:655 (1988); Somkuti et al., *Proc. 4th Eur. Cong. Biotechnology*, 1:412 (1987) *[Streptococcus]*.

Methods for introducing exogenous DNA into yeast cells are well known in the art, and usually include either the transformation of spheroplasts or of intact yeast cells treated with alkali cations. Transformation procedures usually vary with the yeast species to be transformed (Kurtz et al., *Mol. Cell. Biol.* 6:142 (1986); Kunze et al., *J. Basic Microbiol.*, 25:141 (1985) *[Candida]*, Gleeson et al., *J. Gen. Microbiol.*, 132:3459 (1986); Roggenkamp et al., *Mol. Gen. Genet.*, 202: 302 (1986) *[Hansenula]*, Das et al., *J. Bacteriol.*, 158:1165 (1984); De Louvencourt et al., *J. Bacteriol.*, 754:737 (1983);

Van den Berg et al., *Bio/Technology,* 8:135 (1990) [*Kluyveromyces*], Cregg et al., *Mol. Cell. Biol* 5:3376 (1985); Kunze et al., *J. Basic Microbiol.,* 25:141 (1985); U.S. Pat. Nos. 4,837, 148 and 4,929,555 [*Pichia*], Hinnen et al., *Proc. Natl. Acad. Sci. USA,* 75:1929 (1978); Ito et al., *J. Bacteriol.,* 153:163 (1983) [*Saccharomyces*], Beach and Nurse, *Nature,* 300:706 (1981) [*Schizosaccharomyces*], and Davidow et al., *Curr. Genet.,* 10:39 (1985); Gaillardin et al., *Curr. Genet,* 10:49 (1985) [*Yarrowia*]).

Exogenous DNA is conveniently introduced into insect cells through use of recombinant viruses, such as the baculovirus es described herein.

Methods for introduction of polynucleotides into mammalian cells are known in the art and include lipid-mediated transfection, dextran-mediated transfection, calcium phosphate precipitation, polybrene-mediated transfection, protoplast fusion, electroporation, encapsulation of the polynucleotide(s) in liposomes, biollistics, and direct microinjection of the DNA into nuclei. The choice of method depends on the cell being transformed as certain transformation methods are more efficient with one type of cell than another. (Felgner et al., *Proc. Natl. Acad. Sci.,* 84:7413 (1987); Felgner et al., *J. Biol. Chem.,* 269:2550 (1994); Graham and van der Eb, *Virology,* 52:456 (1973); Vaheri and Pagano, *Virology,* 27:434 (1965); Neuman et al., *EMBO J.,* 1:841 (1982); Zimmerman, *Biochem. Biophys. Acta.,* 694:227-(1982); Sanford et al., *Methods Enzymol.,* 217:483 (1993); Kawai and Nishizawa, *Mol. Cell. Biol* 4:1172, (1984); Chaney et al., *Somat. Cell Mol. Genet.,* 12:237 (1986); Aubin et al., *Methods Mol. Biol.,* 62:319 (1997)). In addition, many commercial kits and reagents for transfection of eukaryotic cells are available.

Following transformation or transfection of a nucleic acid into a cell, the cell may be selected for through use of a selectable marker. A selectable marker is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes which render the recipient host cell resistant to drugs such as actinomycin $C_1$, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. (Davies et al., *Ann. Rev. Microbiol.,* 32: 469, (1978)). Selectable markers may also include biosynthetic genes, such as those in the histidine, tryptophan, and leucine biosynthetic pathways. Upon transfection or transformation of a host cell, the cell is placed into contact with an appropriate selection marker.

For example, if a bacterium is transformed with a nucleic acid construct that encodes resistance to ampicillin, the transformed bacterium may be placed on an agar plate containing ampicillin. Thereafter, cells into which the nucleic acid construct was not introduced would be prohibited from growing to produce a colony while colonies would be formed by those bacteria that were successfully transformed. An analogous system may be used to select for other types of cells, including both prokaryotic and eukaryotic cells.

V. Method to Produce Clostripain

Methods to produce clostripain and variants thereof are provided by the invention. The methods involve using an expression cassette of the invention to produce clostripain. Clostripain can be produced in vitro through use of an in vitro transcription and translation system, such as a rabbit reticulocyte lysate or a wheat germ cell-free system. (Stueber et al., *EMBO J.,* 3:3143 (1984)). Preferably clostripain is produced though in vivo expression within a cell into which an expression cassette encoding clostripain has been introduced.

Generally, cells having an expression cassette integrated into their genome or which carry an expression cassette extrachromosomally are grown to high density and then induced. Following induction, the cells are harvested and the expressed clostripain is isolated. Such a system is preferred when an expression cassette includes a repressed promoter. The cells can be induced by many art recognized methods that include, but are not limited to, heat shift, addition of an inducer such as IPTG, or infection by a virus or bacteriophage that causes expression of the expression cassette.

Alternatively, cells that carry an expression cassette having a constitutive promoter do not need to be induced as the promoter is always active. In such systems, the cells are allowed to grow until a desired quantity of clostripain is produced and then the cells are harvested.

Methods and materials for the growth and maintenance of many types of cells are well known and are available commercially. Examples of media that may be used include, but are not limited to: YEPD, LB, TB, 2xYT, GYT, M9, NZCYM, NZYM, NZN, SOB, SOC, Alsever's solution, CHO medium, Dulbecco's Modified Eagle's Medium, and HBSS. (Sigma, St. Louis, Mo.; Sambrook and Russell, Molecular Cloning: A Laboratory Manual, 3rd edition (Jan. 15, 2001) Cold Spring Harbor Laboratory Press, ISBN: 0879695765; Summers and Smith, Texas Agricultural Experiment Station Bulletin No. 1555, (1987)).

TABLE I

Sequence descriptions and SEQ ID NOs: for examples of inclusion body fusion partners (IBFP) and translation initiation sequences (TIS)

| SEQ ID NO | Description | Sequence |
|---|---|---|
| 1 | IBFP | GSGQGQAQYLSASCVVFTNYSGDTASQVD |
| 2 | IBFP | GSGQGQAQYLAASLVVFTNYSGDTASQVD |
| 3 | IBFP | GSYLAASLVVFTNYSGDTASVD |
| 4 | IBFP | GSGQGQAQYLAASLVVFTNYSGD |
| 5 | IBFP | GSYLAASLYVFTNYSGD |
| 6 | IBFP | GSQYLAAVLVVFTNYSGDTASQVD |
| 7 | IBFP | GSGQGQAQYLTASLVKFTNYSGDTASQVD |
| 8 | IBFP | GSGQGQAQYLTASLVQFTNYSGDTASQVD |
| 9 | IBFP | GSGQGQAQYLPASLVKFTNYSGDTASQVD |
| 10 | IBFP | GSGQGQAQYLPASLVQFTNYSGDTASQVD |
| 11 | IBFP | GSGQGQAQYLAASLVKFTNYSGDTASQVD |
| 12 | IBFP | GSGQGQAQYLAASLVQFTNYSGDTASQVD |
| 13 | IBFP | GSGQGQAQYLSASLVKFTNYSGDTASQVD |
| 14 | IBFP | GSGQGQAQYLSASLVQFTNYSGDTASQVD |
| 15 | IBFP | GSGQGQAQYLAAVLVVPTNYSGDTASQVD |
| 16 | IBFP | AEEEEILLEVSLVFKVKEFAPDAPLFTGPAY |
| 17 | T7tag | MASMTGGQ |

TABLE I-continued

Sequence descriptions and SEQ ID NOs: for examples of inclusion body fusion partners (IBFP) and translation initiation sequences (TIS)

| SEQ ID NO | Description | Sequence |
| --- | --- | --- |
| 18 | T7tag | ATGGCTAGCATGACTGGTGGACAG |
| 19 | GST-Tag | MSPILGYWKIKGLVQPTRLLLEYLE |
| 20 | GST-Tag | ATGTCCCCCATACTAGGTTATTGGAAA ATAAAGGGCCTTGTGCAACCCACTCGA CTTCTTTTGGAATATCTTGAA |
| 21 | Lactamase-Tag | MSIQHFRVALIPFFAAFSLPVFA |
| 22 | Lactamase-Tag | ATGAGTATTCAACATTTCCGTGTCGCCC TTATTCCCTTTTTTGCGGCATTTTCCCTT CCTGTTTTTGCT |
| 23 | α-factor | MRFPSIFTAVLFAASSALAAPVNTTTEDE TAQIPAEAVIGYSDLEGDFDVAVLPFSNS TNNGLLFINTTIASIAAKEEGVSLEKR |
| 24 | α-factor | ATGAGATTTCCTTCAATTTTTACTGCA GTTTTATTCGCAGCATCCTCCGCATTA GCTGCTCCAGTCAACACTACAACAGA AGATGAAACGGCACAAATTCCGGCTG AAGCTGTCATCGGTTACTCAGATTTAG AAGGGGATTTCGATGTTGCTGTTTTGC CATTTTCCAACAGCACAAATAACGGG TTATTGTTTATAAATACTACTATTGCC AGCATTGCTGCTAAAGAAGAAGGGGT ATCTCTCGAGAAAAGA |
| 25 | T7 Gene 10 N-Term | MASMTGGQQMGR |

TABLE II

Nucleic acid and amino acid sequences of clostripain

Nucleic acid sequence of full length clostripain (preproclostripain) (1-526)

ATGTTAAGAAGAAAAGTATCAACACTATTAATGA (SEQ ID NO: 26)

CAGCTTTGATAACTACTTCATTTTTAAATTCCAA

ACCCGTATATGCAAATCCAGTAACTAAATCCAAG

GATAATAACTTAAAAGAAGTACAACAAGTTACAA

GCAAGAGTAATAAAAACAAAAATCAAAAAGTAAC

TATTATGTACTATTGCGACGCAGATAATAACTTG

GAAGGAAGTCTATTAAATGATATCGAGGAAATGA

AAACAGGATATAAGGATAGTCCTAATTTAAATTT

AATTGCTCTTGTAGACAGATCCCCAAGATATAGC

AGTGACGAAAAAGTTTTAGGTGAAGATTTTAGTG

ATACACGTCTTTATAAGATTGAAACACAATAAGG

CAAATAGATTAGACGGTAAAAATGAATTTCCAGA

AATAAGTACTACTAGTAAATATGAAGCTAACATG

GGGGATCCTGAAGTTCTTAAAAAATTTATTGATT

TABLE II-continued

Nucleic acid and amino acid sequences of clostripain

ATTGTAAATCTAATTATGAGGCTGATAAATATGT

GCTTATAATGGCTAATCATGGTGGTGGTGCAAGG

GAAAAATCAAATCCAAGATTAAATAGAGCAATTT

GCTGGGATGATAGTAACCTTGATAAAAATGGTGA

AGCAGACTGCCTTTATATGGGTGAAATTTCAGAT

CATTTAACAGAAAAACAATCAGTTGATTTACTTG

CCTTTGATGCGTGCCTTATGGGAACTGCAGAAGT

AGCGTATCAGTATAGACCAGGTAATGGAGGATTT

TCTGCCGATACTTTAGTTGCTTCAAGCCCAGTAG

TTTGGGGTCCTGGATTCAAATATGATAAGATTTT

CGATAGGATAAAAGCTGGTGGAGGAACTAATAAT

GAGGATGATTTAACTTTAGGTGGTAAAGAACAAA

ACTTTGATCCTGCAACCATTACCAATGAGCAATT

AGGTGCATTATTTGTAGAAGAGCAAAGAGACTCA

ACACATGCCAATGGTCGCTATGATCAACACTTAA

GCTTTTATGATTTAAAGAAAGCTGAATCAGTAAA

AAGAGCCATAGATAATTTAGCTGTTAATCTAAGT

AATGAAAACAAAAAATCTGAAATTGAAAAATTAA

GAGGAAGTGGAATTCATACAGATTTAATTGCATT

ACTTCGATGAATATTCTGAAGGAGAATGGGTTGA

ATATCCTTATTTTGACGTGTATGATTTATGTGAA

AAAATAAATAAAAGTGAAAATTTTAGTAGTAAAA

CTAAAGATTTAGCTTCAAATGCTATGAATAAATT

AAATGAAATGATAGTTTATTCTTTTGGAGACCCT

AGTAATAATTTTAAAGAAGGAAAAAATGGATTGA

GTATATTCTTACCTAATGGAGATAAAAAATATTC

AACTTATTATACATCAACCAAGATACCTCATTGG

ACTATGCAAAGTTGGTATAATTCAATAGATACAG

TTAAATATGGATTGAATCCTTACGGAAAATTAAG

TTGGTGTAAAGATGGACAAGATCCTGAAATAAAT

AAAGTTGGAAATTGGTTTGAACTTCTAGATTCTT

GGTTTGATAAAACTAATGATGTAACTGGAGGAGT

TAATCATTACCAATGGTAA

Nucleic acid sequence of mature clostripain (clostripain) (51-526)

AACAAAAATCAAAAGTAACTATTATGTACTATTG (SEQ ID NO: 27)

CGACGCAGATAATAACTTGGAAGGAAGTCTATTA

AATGATATCGAGGAAATGAAAACAGGATATAAGG

ATAGTCCTAATTTAAATTTAATTGCTCTTGTAGA

CAGATCCCCAAGATATAGCAGTGACGAAAAAGTT

TABLE II-continued

Nucleic acid and amino acid sequences of clostripain

TTAGGTGAAGATTTTAGTGATACACGTCTTTATA

AGATTGAACACAATAAGGCAAATAGATTAGACGG

TAAAAATGAATTTCCAGAAATAAGTACTACTAGT

AAATATGAAGCTAACATGGGGGATCCTGAAGTTC

TTAAAAAATTTATTGATTATTGTAAATCTAATTA

TGAGGCTGATAAATATGTGCTTATAATGGCTAAT

CATGGTGGTGGTGCAAGGGAAAAATCAAATCCAA

GATTAAATAGAGCAATTTGCTGGGATGATAGTAA

CCTTGATAAAAATGGTGAAGCAGACTGCCTTTAT

ATGGGTGAAATTTCAGATCATTTAACAGAAAAAC

AATCAGTTGATTTACTTGCCTTTGATGCGTGCCT

TATGGGAACTGCAGAAGTAGCGTATCAGTATAGA

CCAGGTAATGGAGGATTTTCTGCCGATACTTTAG

TTGCTTCAAGCCCAGTAGTTTGGGGTCCTGGATT

CAAATATGATAAGATTTTCGATAGGATAAAAGCT

GGTGGAGGAACTAATAATGAGGATGATTTAACTT

TAGGTGGTAAAGAACAAAACTTTGATCCTGCAAC

CATTACCAATGAGCAATTAGGTGCATTATTTGTA

GAAGAGCAAAGAGACTCAACACATGCCAATGGTC

GCTATGATCAACACTTAAGCTTTTATGATTTAAA

GAAAGCTGAATCAGTAAAAAGAGCCATAGATAAT

TTAGCTGTTAATCTAAGTAATGAAAACAAAAAAT

CTGAAATTGAAAAATTAAGAGGAAGTGGAATTCA

TACAGATTTAATGCATTACTTCGATGAATATTCT

GAAGGAGAATGGGTTGAATATCCTTATTTTGACG

TGTATGATTTATGTGAAAAAATAAATAAAAGTGA

AAATTTTAGTAGTAAAACTAAAGATTTAGCTTCA

AATGCTATGAATAAATTAAATGAAATGATAGTTT

ATTCTTTTGGAGACCCTAGTAATAATTTTAAAGA

AGGAAAAAATGGATTGAGTATATTCTTACCTAAT

GGAGATAAAAAATATTCAACTTATTATACATCAA

CCAAGATACCTCATTGGACTATGCAAAGTTGGTA

TAATTCAATAGATACAGTTAAATATGGATTGAAT

CCTTACGGGAAAATTAAGTTGGTGTAAAGATGGA

CAAGATCCTGAAATAAATAAAGTTGGAAATTGGT

TTGAACTTCTAGATTCTTGGTTTGATAAAACTAA

TGATGTAACTGGAGGAGTTAATCATTACCAATGG

TAA

Amino acid sequence of full length clostripain (preproclostripain)
MLRRKVSTLLMTALITTSFLNSKPVYANPVTKSK (SEQ ID NO: 28)

DNNLKEVQQVTSKSNKNKNQKVTIMYYCDADNNL

EGSLLNDIEEMKTGYKDSPNLNLIALVDRSPRYS

SDEKVLGEDFSDTRLYKIEHNKANRLDGKNEFPE

ISTTSKYEANMGDPEVLKKFIDYCKSNYEADKYV

LIMANHGGGAREKSNPRLNRAICWDDSNLDKNGE

ADCLYGEISDHLTEKQSVDLLAFDACLMGTAEVA

YQYRPGNGGFSADTLVASSPVVWGPGFKYDKIFD

RIKAGGGTNNEDDLTLGGKEQNFDPATITNEQLG

ALFVEEQRDSTHANGRYDQHLSFYDLKKAESVKR

AIDNLAVNLSNENKKSEIEKLRGSGIHTDLMHYF

DEYSEGEWVEYPYFDVYDLCEKINKSENFSSKTK

DLASNAMNKLNEMIVYSFGDPSNNFKEGKNGLSI

FLPNGDKKYSTYYTSTKIPHWTMQSWYNSIDTVK

YGLNTPYGKLSWCKDGQDPEINKVGNWPELLDSW

FDKTNDVTGGVNHYQW

Amino acid sequence of mature clostripain (clostripain) (51-526)
NKNQKVTIMYYCDADNNLEGSLLNDIEEMKTGYK (SEQ ID NO: 29)

DSPNLNLIALVDRSPRYSSDEKVLGEDFSDTRLY

KIEHNKANRLDGKNEFPEISTTSKYEANMGDPEV

LKKFIDYCKSNYEADKYVLIMANHGGGAREKSNP

RLNRAICWDDSNLDKNGEADCLYMGEISDHLTEK

QSVDLLAFDACLMGTAEVAYQYRPGNGGFSADTL

VASSPVVWGPGFKYDKIFDRIKAGGGTNNEDDLT

LGGKEQNFDPATITNEQLGALFVEEQRDSTHANG

RYDQHLSFYDLKKAESVKRAIDNLAVNLSNENKK

SEIEKLRGSGIHTDLMHYFDEYSEGEWVEYPYFD

VYDLCEKINKSENFSSKTKDLASNAMNKLNEMIV

YSFGDPSNNFKEGKNGLSIFLPNGDKKYSTYYTS

TKIPHWTMQSWYNSIDTVKYGLNPYGKLSWCKDG

QDPEINKVGNWFELLDSWFDKTNDVTGGVNHYQW

EXAMPLES

Example 1

E. coli High Yield Expression Vectors

An E. coli high yield nucleic acid construct of the invention is preferably constructed through use of a high copy number vector that is stably maintained within a host cell. Preferably the vector contains an expression cassette having a strong promoter that is operably linked to an open reading frame that encodes clostripain. The vectors pBN115 and pBN121 were constructed according to these considerations. These vectors were constructed through use of the larger DNA fragment produced from restriction enzyme digestion of pGEX2T (Amersham Pharmacia Biotech, Piscataway, N.J.) with FspI-SmaI. This fragment contained the replication origin of pMB1 for high copy number maintenance, the LacIq gene for promoter suppression, the GST terminator for transcription termination, and the bla gene for ampicillin resistance. A strong promoter, Tac, was amplified from the pGEX2T plasmid with restriction enzyme sites at both ends using the following primers:

```
Primer 1:
5' TGC ATT TCT AGA ATT GTG AAT    (SEQ ID NO: 30)

TGT TAT CCG CTC A 3'.

Primer 2:
5' TCA AAG ATC TTA TCG ACT GCA    (SEQ ID NO: 31)

CGG 3'.
```

PCR amplification produced the following product:

```
                                          (SEQ ID NO: 32)
TCAAAGATCTTATCGACTGCACGGTGCACCAATGCTTCTGGCGTCA

GGCAGCCATCGGAAGCTGTGGTATGGCTGTGCAGGTCGTAAATCAC

TGCATAATTCGTGTCGCTCAAGGCGCACTCCCGTTCTGGATAATGT

TTTTTGCGCCGACATCATAACGGTTCTGGCAAATATTCTGAAATGA

GCTGTTGACAATTAATCATCGGCTCGTATAATGTGTGGAAT

TGTGAGCGGATAACAATTCACA]ATTCTAGAAATGCA.
```

The −35 and −10 promoter consensus sequences are bolded and underlined with dots, and the downstream transcriptional start A residue (within the lac operator gene sequence) is bolded and underlined with a solid line. The lac operator sequence is enclosed within brackets. The PCR product of the Tac promoter fragment was ligated into the larger FspI-SmaI fragment from pGEX2T (U.S. Pat. No. 6,316,224).

The ligation mixture was transformed into high efficiency *E. coli* competent cells by heat shock at 42° C. for 45 seconds and streaked on LB+50 μg/ml Ampicillin+Agar plates. Vectors (plasmids) from cultures of single colonies were prepared. A correct vector (plasmid) was identified by restriction enzyme digestion. The XbaI-XhoI fragment from pET23a plasmid (Novagen, Madison, Wis.), which contained the T7 gene 10 ribosome binding site and the T7tag initiation sequence, was inserted into the correct vector identified above at the XbaI-SmaI site of the nucleic acid construct. The resulting vector (plasmid) was named pBN115(Tac). (More information about pBN115 was described in U.S. Pat. No. 6,316,224).

To introduce a kanamycin selection marker, the plasmid pBN115(Tac) was digested with AatII-FspI to remove the 0.7 kb ampicillin resistance gene. A 1.1 kb PCR product, containing the aminophosphotransferase gene that encodes kanamycin resistance, was then cloned into the pBN115(Tac) vector at the AatII-FspI sites. The kanamycin resistance gene was produced through selective PCR amplification of the pCT-Blunt plasmid (Invitrogen, Carlsbad, Calif.) using the following primers:

KANXY1: 5'-CCT GACGTC CCG GAT GAA TGT CAG CTA CTG GGC-3' (AatII site underlined) (SEQ ID NO: 33), KANXY2: 5'-GGC TGCGCA AAG GAG AAA ATA CCG CAT CAG GAA-3' (FspI site underlined) (SEQ ID NO: 34).

The resulting plasmid was designated as pBN121(Tac), and *E. coli* that were transformed with this plasmid could be selected in LB+25 μg/ml kanamycin media Like plasmid pBN115(Tac), pBN121 contains unique NheI and XhoI restriction sites for inserting the foreign gene sequence to be expressed, such as the gene sequence that encodes clostripain.

Example 2

Cloning of the Prepro-Clostripain(1-526)

The prepro-clostripain(1-526) gene was PCR amplified from the *C. histolyticum* genome by using Pfu DNA polymerase (Stratagene, La Jolla, Calif.) and the following primers:

0925CLA: 5'-AGA GCT CATATG TTA AGA AGA AAA GTA TCA ACA CTA TTA ATG-3' (NdeI site underlined) (SEQ ID NO: 35) and 0925CLB: 5'-TTG CTC GAG TTA CCA TTG GTA ATG ATT AAC TCC TCC AGT-3' (XhoI site underlined) (SEQ ID NO: 36).

The genomic DNA template was prepared by repeated phenol-chloroform extraction and ethanol precipitation of *C. histolyticum* Collagenase (Worthington, Lakewood, N.J.). The PCR product was blunt-end inserted into linearized pCR-Blunt vector using the Zero Blunt cloning kit (Invitrogen), and produced the pCR-Blunt-preproClos(1-526) plasmid. The cloned clostripain gene was confirmed by DNA sequencing. FIG. 1 provides the open reading frame of the cloned prepro-clostripain(1-526) gene with some restriction enzyme sites indicated.

The NdeI-XhoI fragment of the prepro-clostripain(1-526) gene from the above pCR-Blunt-preproClos(1-526) plasmid was cloned into the pET23a expression vector (Novagen) at NdeI-XhoI sites to produce a nucleic acid construct. The resulting nucleic acid construct pET23a-preproClos(1-526) was transformed into *E. coli* BL21(DE3) cells, colonies were grown in LB+100 μg/ml ampicillin media. The correct nucleic acid construct was identified by restriction enzyme digestion and DNA sequencing. Glycerol stocks of the *E. coli* host cells harboring the construct were stored at −80° C. or below with 15% glycerol.

Example 3

Cloning of the Pro-Clostripain (28-526)

A DNA fragment containing pro-clostripain (28-526) was amplified by PCR using the pCR-Blunt-preproClos(1-526) plasmid as template and the following primers CLOSPRO (5'-TAT ACATATGAA TCC AGT AAC TAA ATC CAA GGA TAA TAA C-3'; NdeI site underlined) (SEQ ID NO: 37) and, CLOSPRIM2 (5'-CCT AGGATCCCC CAT GTT AGC TTC ATA TTT ACT-3'; BamHI site underlined) (SEQ ID NO: 38).

The amplified fragment had the ATG start codon at the N-terminus of the pro-clostripain (28-526). The PCR product was cleaved with the restriction enzymes NdeI-BamHI and inserted using the same enzymes into the pET23a-preproClos (1-526) nucleic acid construct (Example 2) to produce the pET23a-proClos(28-526) nucleic acid construct. The nucleic acid construct was transformed into *E. coli* HM174(DE3) and BL21(DE3). The correct nucleic acid construct was selected in LB+100 µg/ml ampicillin media Glycerol stocks of the construct were stored as in Example 2.

Example 4

Cloning of Clostripain (51-526)

To prepare a clostripain nucleic acid construct lacking the sequence encoding the pre-propeptide, a PCR amplification reaction was carried out using the pCR-Blunt-preproClos(1-526) plasmid as the template and the following primers:

CLOSPRIM7 (5'-TAT ACATATGAA CAA AAA TCA AAA AGT AAC TAT TAT G-3'; NdeI site underlined) (SEQ ID NO: 39) and CLOSPRIM2 (5'-CCT AGGATCCCC CAT GTT AGC TTC ATA TTT ACT-3'; BamHI site underlined) (SEQ ID NO: 38). (as in Example 3)

The amplified fragment contained the ATG start codon at the N-terminus of clostripain (51-526). The PCR product was cleaved with the restriction enzymes NdeI-BamHI and inserted using the same enzymes into the pET23a-preproClos (1-526) nucleic acid construct (Example 2) to produce the pET23a-Clos(51-526) nucleic acid construct. The pET23a-Clos(51-526) nucleic acid construct was transformed into *E. coli* BL21(DE3) or BL21(DE3)pLysS cells. The correct construct was selected in LB+100 µg/ml ampicillin media Glycerol stocks of the construct were saved as in Example 2.

The NdeI-XhoI fragment from pET23a-Clos(51-526), which contained, the clostripain (51-526) gene, was inserted into the pET24a vector (Novagen) at the NdeI-XhoI sites to produce the pET24a-Clos(51-526) nucleic acid construct. The pET24a-Clos(51-526) nucleic acid construct was transformed into *E. coli* BL21(DE3) or BL21(DE3)pLysS cells. The correct construct was selected in LB+25 µg/ml kanamycin media and glycerol stocks of the construct were saved.

The NdeI-XhoI fragment from pET23a-Clos(51-526) was also inserted into the pBN121(Tac) plasmid (Example 1) at the NdeI-XhoI site to produce the pBN121(Tac)-Clos(51-526) nucleic acid construct. This construct was transformed into *E. coli* BL21 cells. The correct construct was selected in LB+25 µg/ml kanamycin media and glycerol stocks of the construct were saved.

Example 5

Cloning of the T7tag-Clostripain (51-526)

To achieve a higher expression level of clostripain in *E. coli*, a short (8 aa) peptide (T7tag) carrying a strong translation initiation signal from a highly expressed gene, T7 gene 10, was fused to clostripain (51-526) at its N-terminus to optimize clostripain translation. The DNA fragment coding the T7tag-clostripain (51-526) was PCR-amplified using the pCR-Blunt-preproClos(1-526) plasmid as the template and the following primers:

CLOSPRIM2 (5'-CCT AGGATCCCC CAT GTT AGC TTC ATA TTT ACT-3'; BamHI site underlined) (SEQ ID NO: 38). (same as in Example 3) and CLOSPRIM1 (5'-ATA CATATG GCTAGC ATG ACT GGT GGA CAG AAC AAA AAT CAA AAA GTA ACT ATT ATG-3'; (SEQ ID NO: 40); NdeI and NheI sites underlined).

The amplified fragment contained the T7tag sequence at the N-terminal of clostripain (51-526) light chain (FIG. 2). The PCR product was cleaved with restriction enzymes NdeI-BamHI and inserted using the same enzymes into pET24a-Clos(51-526) nucleic acid construct (Example 4) to produce the pET24a-T7tag-Clos(51-526) nucleic acid construct. This construct was transformed into *E. coli* BL21(DE3) cells. Transformants were selected in LB+25 µg/ml kanamycin media and glycerol stocks of cells containing the correct construct were saved as in Example 2.

The NdeI-XhoI fragment from pET24a-T7tag-Clos(51-526), which contained the T7tag-clostripain (51-526) gene, was inserted into the pBN115(Tac) nucleic acid construct (Example 1) at the NdeI-XhoI site to produce the pBN115 (Tac)-T7tag-Clos(51-526) nucleic acid construct. This construct was transformed into *E. coli* BL21 cells. Transformants were selected in LB+100 µg/ml ampicillin media and glycerol stocks of cells containing the correct construct were saved.

In order to introduce a kanamycin selection feature into pBN115/tac-T7tagclos(51-526), the construct was further modified by the method described Example 1. The resulting construct was designated pBN121(Tac)-T7tag-Clost(51-526) (FIG. 3). This construct was transformed into *E. coli* BL21 cells. Transformants were selected in LB+25 µg/ml kanamycin media and glycerol stocks of cells containing the correct construct were saved.

Example 6

Cloning of Clostripain (51-526) with Mutations in the Nonapeptide Linker Region The clostripain core protein is composed of light and heavy chain subunits linked by a nonapeptide into a single polypeptide chain. The nonapeptide is preceded by an Arg residue (Arg$^{181}$ at the C-terminal end of the light chain), ends with an Arg residue (Arg$^{190}$), and contains another Arg residue inside the nanopeptide (Arg$^{187}$). These residues could provide cleavage sites that are used during the maturation of the protein.

Two constructs were designed to mutate the nonapeptide linker region. One contained the entire nonapeptide region, but had all three Arg residues (Arg$^{181}$, Arg$^{187}$, Arg$^{190}$) changed to Gln; the other carried a deletion of the entire nonapeptide, with the mutation Arg$^{181}$ to Gln. In order to introduce mutations into region encoding the linker nonapeptide, a SacI site was inserted at the C-terminus of the light chain by PCR using the pCR-Blunt-Clos(1-526) plasmid (Example 2) as a template and the following primers:

CLOSPRIM6 (5'-TTC CTGAGCTCC ACC ACC ATG ATT AGC CAT TAT AAG-3'; SacI site underlined) (SEQ ID NO: 41) and CLOSPRIM7 (5'-TAT ACATATGAA CAA AAA TCA AAA AGT AAC TAT TAT G-3'; NdeI site underlined) (SEQ ID NO: 39) (as in Example 4).

The amplified DNA fragment was cleaved with the restriction enzymes NdeI-SacI and inserted using the same enzymes into pET24a, to create the nucleic acid construct pET24a-Clos(51-sac).

The three Arg to Gln mutations were then introduced into the nonapeptide linker region by PCR using the pCR-Blunt-Clos(1-526) plasmid (Example 2) as template and the following primers:

CLOSPRIM5 (5'-GGT GGA GCT cag GAA AAA TCA AAT CCA cag TTA AAT cag GCA-3'; SacI site underlined, Gln codon "cag" in lowercase) (SEQ ID NO: 42) and 0925CLB: 5'-TTG CTCGAG TTA CCA TTG GTA ATG ATT AAC TCC TCC AGT-3' (XhoI site underlined) (SEQ ID NO: 36) (as in Example 2).

The PCR product contained the mutated nonapeptide region (R181Q, R187Q and R190Q) and the heavy chain (191-526) (FIG. 4). The PCR product was cleaved with the restriction enzymes SacI-HindIII and inserted using the same enzymes into the pET24a plasmid (Novagen) to create the nucleic acid construct pET24a-Clos(51-HindIII). A 540 bp BamHI-HindIII fragment from the pET24a-Clos(51-HindIII construct, which carried the three intended Arg to Gln mutations in the nonapeptide was cloned into the pET23a-Clos (51-526) construct to replace the fragment containing the wild-type nonapeptide sequence. The resulting nucleic acid construct was designated pET23a-Mclos(51-526, R181Q, R187Q, R190Q), and was transformed into E. coli HMS174 (DE3) cells. Transformants were selected in LB+50 µg/ml ampicillin media and glycerol stocks of cells containing the correct construct were saved as in Example 2.

The nonapeptide deletion mutant was constructed by PCR using the pCR-Blunt-preproClost(1-526) as template and the following primers:

CLOSPRIM8 (5'-GGT GGAGCTCAG gca ATT TGC TGG GAT GAT AGT-3'; SacI site underlined, the Ala$^{191}$ codon "gca" in lowercase) (SEQ ID NO: 43) and 0925CLB: 5'-TTG CTCGAG TTA CCA TTG GTA ATG ATT AAC TCC TCC AGT-3' (XhoI site underlined) (SEQ ID NO: 36). (as in Example 2).

As shown in the CLOSPRIM8 nucleotide sequence, the codon AGG for Arg$^{181}$ was changed to CAG, a codon encoding Gln, which was followed immediately by Ala$^{191}$, the first residue of the heavy chain. Thus, the entire nonapeptide coding sequence was deleted, but the light chain and heavy chain was linked by an Ala. The PCR product was cleaved with SacI-XhoI and inserted into pET24a-Clos(51-Sac) to produce the pET24a-Clos(51-526, A[182-190], R181Q) nucleic acid construct. This construct was transformed into an *E. coli* BL21 (DE3) strain and a BL21(DE3)pLysS. Tranformants were selected in LB+25 μg/ml kanamycin media and glycerol stocks of cells containing the correct construct were saved.

Example 7

*E. coli* Shaking Culture Expression of Various Constructs

LBA media (LB+ampicillin) were used when expressing the pET23a or pBN115 derived nucleic acid constructs. LBK media (LB+kanamycin) were used when expressing the pET24a or pBN121(Tac) derived constructs. Shaking flask cultures of 5 ml LBA or LBK media were started from single colonies of the transformed cells. Shaking flask cultures in 5 ml to 500 ml LBA or LBK media (inoculated by 100 μl to 10 ml overnight culture) were grown at 37° C. and 220 rpm to an $A_{600}$ of 0.5-1.0. Polypeptide expression was induced by addition of IPTG (1 mM final concentration). Cultures were induced for 2 to 8 hours. Samples were taken from cells having the same $A_{600}$ of pre- and post-induced cells. Cells were pelleted and then lysed in distilled water or 10 mM Tris, pH 8 by sonication. The lysate was then centrifuged to separate insoluble and soluble proteins.

The supernatant (soluble protein) from the cell lysate was mixed 1:1 with 2×SDS-PAGE sample buffer. The pellets were resuspended directly in 1×SDS-PAGE sample buffer. These samples were resolved by SDS-PAGE (Invitrogen) according to the manufacturer's instructions and stained with Coomassie Brilliant Blue.

*E. coli* BL21 cells transformed with pBN121(Tac)-T7tag-Clos(51-526) produced an insoluble protein of 60 kDa upon IPTG induction, corresponding to the calculated size of the 484 amino acid encoded by the T7tag-clostripain(51-526) construct. BL21 cells transformed with pBN121(Tac)-Clos (51-526) also produced an insoluble protein that was 59 kDa. This protein corresponded in size to the 476 amino acid clostripain (51-526) encoded by the construct. The T7tag sequence markedly increased the expression yield of the recombinant clostripain (51-526) (FIG. 5).

Example 8

*E. coli* Fermentation Production of T7tag-Clostripain (51-526)

Expression of the T7tag-clostripain by *E. coli* BL21 cells transformed with the pBN121(Tac)-T7tag-Clos(51-526) nucleic acid construct was evaluated in 5 L or larger fermentation. A 100 μl glycerol stock of the construct was used to inoculate 100 ml LB+25 μg/ml Kanamycine media in a shaking flask. The shaking culture was grown in a rotary shaker at 37° C. until the $A_{540}$ reached 1.5±0.5. The contents of the shaking flask culture were then used to inoculate a 5 L fermentation tank containing a defined minimal media (e.g. M9 media, Molecular Cloning, 2$^{nd}$ edition, Sambrook et al). Glucose served as the carbon source and was maintained at below 4%. About 10 μg/ml kanamycin was used in the fermentation. Dissolved oxygen was controlled at 40% by cascading agitation and aeration with additional oxygen. Ammonium hydroxide solution was fed to control the pH at about 6.9 and to supply additional nitrogen. The cells were induced with IPTG at a final concentration of 0.1-1 mM after the $A_{540}$ reached 50-75 for 2-6 hours. After the induction was complete, the cells were cooled and harvested by centrifugation. The cell sediments were stored at a temperature below −20° C. or were lysed immediately for use. Cells, after thawing if they were frozen, are resuspended in distilled water, then lysed by sonication or homogenization. The lysate was centrigued to pellet inclusion bodies of the expressed polypeptide. The polypeptide sediments were dissolved in 8M urea for further treatment.

Example 9

Clostripain Activation and Activity Assay

Clostripain-containing inclusion bodies isolated from 1 $OD_{600}$ of IPTG-induced cells were solubilized in 50 μL of 8 M urea and maintained in 4 M urea at 4° C. after removal of the insoluble fraction by centrifugation. Activation was carried out by diluting the clostripain solution (in 8 M urea) into activation buffer containing 50 mM Tris-HCl (pH 7.6), 10 mM DTT, 1 mM $CaCl_2$, and 2M urea (final concentration) at room temperature and incubating for 1 hr.

The activity assay was conducted at the same temperature by mixing 10 μL of the activated clostripain with 1 ml of assay buffer containing 50 mM Tris -HCl (pH 7.6), 10 mM DTT, 5 mM $CaCl_2$, and 67 μg/ml N-carbobenzoxy-L -arginine p-nitroanilide (BAPNA). After incubation for 10 min, release of p-nitroaniline was followed spectrophotometrically by measuring the increase in absorbance at 410 nm.

The inclusion bodies of T7tag-clostripain (51-526) polypeptide were rapidly refolded and converted into active clostripain enzyme through use of the procedure described above. Upon activation, the nonapeptide linker was removed and the T7tag-clostripain (51-526) polypeptide was converted into a heavy chain of 43 kDa and a light chain of 16 kDa, the latter contained 8 amino acids of T7tag (FIG. 6). Surprisingly, full clostripain activity was still retained when the T7tag sequence was linked to the N-terminus of the light chain. Other polypeptides containing clostripain (51-526) were activated with less efficiency by the same procedure.

The concentration of the chaotropic agent played a role in the activation procedure. For example, when less that 3 M urea was used in the activation buffer, optimal clostripain activity was obtained. Guanidine inhibited the activation of clostripain.

Materials

Plasmids and Bacterial Strains

The plasmid vector pCR-Blunt was from Invitrogen (Carlsbad, Calif.). pGEX-2T was from Pharmacia Biotech (Piscataway, N.J.). *E. coli* strains BL21, BL21(DE3), BL219 (DE3)pLysS, HMS174, and HMS174(DE3) were from Novagen (Madison, Wis.); *E. coli* strain Top10 was from Invitrogen. *C. histolyticum*-derived collagenase, used as the source of the clostripain gene for PCR amplification, was purchased from Worthington Biochemical (Lakewood, N.J.).

DNA Modification Enzymes and Purification Kits

Restriction endonucleases and calf intestinal alkaline phosphatase (CIP) were purchased from New England Biolabs (Beverly, Mass.). PCR primers were prepared by Operon Technologies (Alameda, Calif.). Pfu DNA polymerase and Taq DNA polymerase were purchased from Stratagene (La Jolla, Calif.) and Promega (Madison, Wis.), respectively. T4 DNA ligase was from Life Technologies (Rockville, Md.). The QIAquick PCR Purification kit and QIAprep Spin Miniprep kit were from QIAGEN (Valencia, Calif.).

DNA Polymerase Chain Reaction (PCR)

The PCR amplification reaction was carried out in PCR reaction buffer (20 mM Tris-HCl (pH 8.8), 2 mM $MgSO_4$, 10 mM KCl, 10 mM $(NH_4)_2SO_4$, 1% Triton X-100, 100 µg/ml nuclease-free BSA) containing primers (0.4 µM) and dNTP (1.0 mM) for 30 cycles of 94° C. for 45 s, 55° C. for 45 s, and 72° C. for 45 s to 5 min, depending on the size of the DNA fragment PCR products were purified using the QIAquick PCR Purification kit. PCR primers were from Operon Technologies (Alameda, Calif.).

REFERENCES

Alberts et al., Molecular Biology of the Cell, 2nd ed., 1989.
Amann et al., *Gene*, 25:167 (1983).
Amann et al., *Gene*, 40:183 (1985).
Aubin et al., *Methods Mol. Biol.*, 62:319 (1997).
Augustin et al., *FEMS Microbiol. Lett.*, 66:203 (1990).
Ausubel et al., Current Protocols in Molecular Biology, Green Publishing Associates and Wiley Interscience, NY. (1989).
Barany et al., *J. Bacteriol.*, 144:698 (1980).
Beach and Nurse, *Nature*, 300:706 (1981).
Beaucage and Caruthers, *Tetra. Letts.*, 22:1859 (1981).
Birnstiel et al., *Cell*, 41:349 (1985).
Boshart et al., *Cell*, 41: 521 (1985).
Botstein, et al., *Gene*, 8:17 (1979).
Brake et al., *Proc. Natl. Acad. Sci. USA*, 81:4642 (1984).
Butt et al., *Microbiol. Rev.*, 51:351 (1987).
Carbonell et al., *Gene*, 73: 409 (1988).
Carbonell et al., *J. Virol.*, 56:153 (1985).
Chaney et al., *Somat. Cell Mol. Genet.*, 12:237 (1986).
Chang et al., *Nature*, 198:1056 (1977).
Chassy et al., *FEMS Microbiol. Lett.*, 44:173 (1987).
Cohen et al., *Proc. Natl. Acad. Sci. USA*, 69:2110 (1973).
Cohen et al., *Proc. Natl. Acad. Sci. USA*, 77: 1078 (1980).
Cregg et al., *Mol. Cell. Biol.*, 5:3376 (1985).
Das et al., *J. Bacteriol.*, 158:1165 (1984).
Davidow et al., *Curr. Genet.*, 10:39 (1985).
Davies et al., *Ann. Rev. Microbiol.*, 32: 469, (1978).
de Boer et al., *Proc. Natl. Acad. Sci. USA*, 80: 21 (1983).
De Louvencourt et al., *J. Bacteriol.*, 154:737 (1983).
De Louvencourt et al., *J. Bacteriol.*, 754:737 (1983).
Dijkema et al., *EMBO J.*, 4:761 (1985).
Dower et al., *Nuc. Acids Res.*, 16:6127 (1988).
Felgner et al., *J. Biol. Chem.*, 269:2550 (1994).
Felgner et al., *Proc. Natl. Acad. Sci.*, 84:7413 (1987).
Fiedler et al., *Anal. Biochem*, 170:38 (1988).
Franke and Hruby, *J. Gen. Virol.*, 66:2761 (1985).
Fraser et al., *In Vitro Cell. Dev. Biol.*, 25:225 (1989).
Freifelder, Physical Biochemistry: Applications to Biochemistry and Molecular Biology, W.H. Freeman and Co., 2nd editions New York, N.Y. (1982).
Friesen et al., "The Regulation of Baculovirus Gene Expression", in: The Molecular Biology of Baculoviruses (ed. Walter Doerfler), 1986.
Gaillardin et al., *Curr. Genet.*, 10:49 (1985).
Ghrayeb et al., *EMBO J.*, 3: 2437 (1984).
Gleeson et al., *J. Gen. Microbiol.*, 132:3459 (1986).
Gluzman, *Cell*, 23:175 (1981).
Goeddel et al., *N.A.R.*, 8: 4057 (1980).
Gorman et al., *Proc. Natl. Acad. Sci. USA*, 79:6777 (1982b).
Graham and van der Eb, *Virology*, 52:456 (1973).
Gregor and Proudfoot, *EMBO J.*, 17:4771 (1998).
Guan et al., *Gene* 67:21 (1997).
Harlander, "Transformation of *Streptococcus lactis* by electroporation", in: Streptococcal Genetics (ed. J. Ferretti and R. Curtiss III), 1987.
Harlow and Lane, Antibodies: A Laboratory Manual, Cold Spring Harbor Laboratory Press, Cold Spring Harbor, N.Y. (1988).
Henikoff et al., *Nature*, 283:835 (1981).
Hinnen et al., *Proc. Natl. Acad. Sci. USA*, 75:1929 (1978).
Hollenberg et al., "The Expression of Bacterial Antibiotic Resistance Genes in the Yeast *Saccharomyces cerevisiae*", in: Plasmids of Medical, Environmental and Commercial Importance (eds. K N. Timmis and A. Puhler), 1979.
Hollenberg et al., *Curr. Topics Microbiol. Immunol.*, 96: 119 (1981).
Ito et al., *J. Bacteriol.*, 153:163 (1983).
Kaufman et al., *Mol. Cell. Biol.*, 9:946 (1989).
Kawai and Nishizawa, *Mol. Cell. Biol.*, 4:1172 (1984).
King and Possee, The baculovirus expression system. A laboratory guide. Chapman and Hall, London, England (1992).
Kunkel et al., *Methods in Enzymol.*, 154:367 (1987).
Kunkel, *Proc. Natl. Acad. Sci. USA*, 82:488 (1985).
Kunze et al., *J. Basic Microbiol.*, 25:141 (1985).
Kurtz et al., *Mol. Cell. Biol.*, 6:142 (1986).
Kushner, "An improved method for transformation of *Escherichia coli* with ColE1-derived plasmids", in: Genetic Engineering: Proceedings of the International Symposium on Genetic Engineering (eds. H. W. Boyer and S. Nicosia), 1978.

Lebacq-Verheyden et al., *Mol. Cell. Biol.,* 8: 3129 (1988).
Lewin, Genes VII, Oxford University Press, New York, N.Y. (2000).
Lopez-Ferber et al., *Methods Mol. Biol.,* 39:25 (1995).
Luckow and Summers, *Virology* 17:31 (1989).
Maeda et al., *Nature,* 315:592 (1985).
Mandel et al., *J. Mol. Biol.,* 53: 159 (1970).
Maniatis et al., *Science,* 236:1237 (1987).
Martin et al., *DNA,* 7: 99 (1988).
Marumoto et al., *J. Gen. Virol.,* 68:2599 (1987).
Masson et al., *FEMS Microbiol. Lett.,* 60:273 (1989).
Masui et al., in: Experimental Manipulation of Gene Expression, (1983).
McCarroll and King, *Curr. Opin. Biotechnol.,* 8:590 (1997).
Mercerau-Puigalon et al., *Gene,* 11:163 (1980).
Miller et al., *Ann. Rev. Microbiol.,* 42:177 (1988).
Miller et al., *Bioessays,* 4:91 (1989).
Miller et al., *Proc. Natl. Acad. Sci. USA,* 8:856 (1988).
Miyajima et al., *Gene,* 58: 273 (1987).
Myanohara et al., *Proc. Natl. Acad. Sci. USA,* 80: 1 (1983).
Neuman et al., *EMBO J.,* 1:841 (1982).
Oka et al., *Proc. Natl. Acad. Sci. USA,* 82: 7212 (1985).
O'Reilly et al., Baculovirus expression vectors: a laboratory manual. W.H. Freeman & Company, New York, N.Y. (1992).
Orr-Weaver et al., *Methods in Enzymol.,* 101:228 (1983).
Palva et al., *Proc. Natl. Acad. Sci. USA,* 79:5582 (1982).
Panthier et al., *Curr. Genet.,* 2:109 (1980).
Perry et al., *Infec. Immun.,* 32:1295 (1981).
Powell et al., *Appl. Environ. Microbiol.,* 54:655 (1988).
Proudfoot and Whitelaw, "Termination and 3' end processing of eukaryotic RNA", in: Transcription and Splicing (eds. B. D. Hames and D. M. Glover) 1988.
Proudfoot, *Trends Biochem. Sci.,* 14:105 (1989).
Raibaud et al., *Ann. Rev. Genet.,* 18:173 (1984).
Richardson, *Crit. Rev. Biochem. Mol. Biol.,* 28:1 (1993).
Rine et al., *Proc. Natl. Acad. Sci. USA,* 80:6750 (1983).
Roggenkamp et al., *Mol. Gen. Genet.,* 202:302 (1986).
Sambrook and Russell, Molecular Cloning: A Laboratory Manual, 3rd edition (Jan. 15, 2001) Cold Spring Harbor Laboratory Press, ISBN: 0879695765.
Sambrook et al., "Expression of Cloned Genes in Mammalian Cells", in: Molecular Cloning: A Laboratory Manual, 2nd ed., 1989.
Sanford et al., *Methods Enzymol.,* 217:483 (1993).
Sassone-Corsi and Borelli, *Trends Genet.,* 2:215 (1986).
Shimatake et al., *Nature,* 292:128 (1981).
Shimizu et al., *Mol. Cell. Biol.,* 6:1074 (1986).
Shine et al., *Nature,* 254: 34 (1975).
Smith et al., *Mol. Cell. Biol.,* 3: 2156 (1983).
Smith et al., *Proc. Natl. Acad. Sci. USA,* 82: 8404 (1985).
Somkuti et al., *Proc. 4th Eur. Cong. Biotechnology,* 1:412 (1987).
Steitz et al., "Genetic signals and nucleotide sequences in messenger RNA", in: Biological Regulation and Development: Gene Expression (ed. R. F. Goldberger) (1979).
Stinchcomb et al., *J. Mol. Biol.,* 158:157 (1982).
Studier et al., *J. Mol. Biol.,* 189: 113 (1986).
Stueber et al., *EMBO J.,* 3:3143 (1984).
Tabor et al., *Proc. Natl. Acad. Sci. USA,* 82:1074 (1985).
Taketo, *Biochim. Biophys. Acta,* 949:318 (1988).
Vaheri and Pagano, *Virology,* 27:434 (1965).
van den Berg et al., *Bio/Technology,* 8:135 (1990).
Van den Berg et al., *Bio/Technology,* 8:135 (1990).
Vlak et al., *J. Gen. Virol.,* 69: 765 (1988).

Walker and Gaastra, eds. (1983) *Techniques in Molecular Biology* (MacMillan Publishing Company, New York).
Walsh, Proteins Biochemistry and Biotechnology, John Wiley & Sons, LTD., West Sussex, England (2002).
Wang et al., *J. Bacteriol.,* 172:949 (1990).
Watson, Molecular Biology of the Gene, 4th edition, Benjamin/Cummings Publishing Company, Inc., Menlo Park, Calif. (1987).
Weissmann, "The cloning of interferon and other mistakes", in: Interferon 3 (ed. I. Gresser), 1981.
Wright, *Nature,* 321: 718 (1986).
Yelverton et al., *N.A.R.,* 9: 731 (1981).
Zhao et al., *Microbiol. Mol. Biol. Rev.,* 63:405 (1999).
Zimmerman, *Biochem. Biophys. Acta.,* 694:227 (1982).
EPO Publ. No. 012 873.
EPO Publ. No. 036 259.
EPO Publ. No. 036 259.
EPO Publ. No. 036 776.
EPO Publ. No. 036 776.
EPO Publ. No. 060 057.
EPO Publ. No. 063 953.
EPO Publ. No. 063 953.
EPO Publ. No. 121 775.
EPO Publ. No. 127 328.
EPO Publ. No. 127 839.
EPO Publ. No. 136 829.
EPO Publ. No. 136 907.
EPO Publ. No. 155 476.
EPO Publ. No. 164 556.
EPO Publ. No. 267 851.
EPO Publ. No. 284 044.
EPO Publ. No. 329 203.
JPO Publ. No. 62,096,086.
PCT Pub. No. WO 89/046699.
PCT Pub. No. WO 84/04541.
PCT Pub. No. WO 84/04541.
U.S. Pat. No. 4,551,433.
U.S. Pat. No. 4,588,684.
U.S. Pat. No. 4,689,406.
U.S. Pat. No. 4,738,921.
U.S. Pat. No. 4,745,056).
U.S. Pat. No. 4,837,148.
U.S. Pat. No. 4,873,192.
U.S. Pat. No. 4,876,197.
U.S. Pat. No. 4,880,734.
U.S. Pat. No. 4,929,555.
U.S. Pat. No. 4,336,336.
U.S. Pat. No. 6,316,224.

All publications, patents and patent applications including priority patent application Ser. No. 60/383,357 filed on May 24, 2002 are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to produce active clostripain comprising:
   (a) incubating an *Escherichia coli* cell containing an expression cassette under conditions that cause the cell to produce clostripain inclusion bodies, wherein the expression cassette comprises a promoter operably linked to an open reading frame that encodes a peptide consisting of a tag linked to clostripain, wherein the tag is selected from the group consisting of SEQ ID NOs:17 and 25, and wherein the clostripain is selected from the group consisting of SEQ ID NO:28, amino acids 28-526 of SEQ NO:28, SEQ ID NO:29, and a variant of SEQ ID NO:29, wherein the variant of SEQ ID NO:29 has at least 98% sequence identity to SEQ II) NO:29;
   (b) harvesting the clostripain inclusion bodies from the *Escherichia coli* cell; and
   (c) solubilizing the clostripain inclusion bodies in an 8 M urea solution; and
   (d) diluting said urea solution to a final solution to a final urea concentration of less than 3 M to produce active clostripain.

2. The method of claim 1, wherein the promoter is a regulatable promoter or a constitutive promoter.

3. The method of claim 1, wherein the promoter is a tac promoter, a T5 promoter, a T7 promoter, a trp promoter, a lac promoter, a lambda phage PL promoter, a heat shock promoter, or a Chlorella Virus promoter.

4. The method of claim 1, wherein the tag is SEQ ID NO:17.

5. The method of claim 1, wherein the tag is SEQ ID NO:25.

6. The method of claim 1, wherein the expression cassette is chromosomally integrated.

7. The method of claim 1, wherein the promoter is an inducible promoter.

8. The method of claim 1, wherein the expression cassette further comprises an enhancer.

9. The method of claim 1, wherein the expression cassette further comprises a signal sequence.

10. The method of claim 9, wherein the tag is SEQ ID NO: 17 and the clostripain is SEQ ID NO: 29.

11. The method of claim 1, wherein the diluting step includes addition of an activation buffer comprising Tris-HCl, DTT, and $CaCl_2$.

12. The method of claim 11 wherein the activation buffer comprises 50 mM Tris-HCl (pH 7.6), 10mM DTT and 1 mM $CaCl_2$.

13. The method of claim 1, wherein the clostripain is solubilized in 8 M urea and the final urea concentration is 2M.

14. A method for producing an activated clostripain comprising:
   (a) producing clostripain inclusion bodies in an *Escherichia coli* cell containing an expression cassette comprising a promoter operably linked to an open reading frame that encodes a peptide consisting of a tag linked to clostripain, wherein the tag is selected from the group consisting of SEQ ID NOs:17 and 25, and wherein the clostripain is selected from the group consisting of SEQ ID NO:28, amino acids 28-526 of SEQ ID NO:28, SEQ ID NO:29, and a variant of SEQ ID NO:29, wherein the variant of SEQ ID NO:29 has at least 98% sequence identity to SEQ ID NO:29;
   (b) harvesting the clostripain inclusion bodies from a fermentation mixture comprising the *Escherichia coli* cell;
   (c) solubilizing the clostripain inclusion bodies in a solution comprising 8M urea; and
   (d) activating the solubilized clostripain by diluting the solution to a final urea concentration of less than 3 M in a metal ion containing buffer.

15. The method of claim 14, wherein the buffer includes $CaCl_2$.

16. The method of claim 14, wherein upon solubilization of the clostripain inclusion bodies, the solution is centrifuged and the solubilized clostripain is thereafter recovered in the centrifugation supernatant.

17. The method of claim 14, wherein the tag is SEQ ID NO: 17.

18. The method of claim 17, wherein the clostripain is SEQ ID NO: 29.

* * * * *

UNITED STATES PATENT AND TRADEMARK OFFICE
CERTIFICATE OF CORRECTION

PATENT NO. : 8,003,362 B2  
APPLICATION NO. : 10/997697  
DATED : August 23, 2011  
INVENTOR(S) : Fred W. Wagner et al.

Page 1 of 1

It is certified that error appears in the above-identified patent and that said Letters Patent is hereby corrected as shown below:

Column 69, Line 25, "...identity to SEQ II) NO:29;" should read --identity to SEQ ID NO:29--

Signed and Sealed this
Twenty-ninth Day of November, 2011

David J. Kappos  
*Director of the United States Patent and Trademark Office*

SEQUENCE LISTING

<160> NUMBER OF SEQ ID NOS: 48

<210> SEQ ID NO 1
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 1

Gly Ser Gly Gln Gly Gln Ala Gln Tyr Leu Ser Ala Ser Cys Val Val
1               5                   10                  15

Phe Thr Asn Tyr Ser Gly Asp Thr Ala Ser Gln Val Asp
            20                  25

<210> SEQ ID NO 2
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 2

Gly Ser Gly Gln Gly Gln Ala Gln Tyr Leu Ala Ala Ser Leu Val Val
1               5                   10                  15

Phe Thr Asn Tyr Ser Gly Asp Thr Ala Ser Gln Val Asp
            20                  25

<210> SEQ ID NO 3
<211> LENGTH: 24
<212> TYPE: PRT
<213> ORGANISM: Artificial Sequence
<220> FEATURE:
<223> OTHER INFORMATION: A synthetic inclusion body fusion partner.

<400> SEQUENCE: 3

Gly Ser Gln Tyr Leu Ala Ala Ser Leu Val Val Phe Thr Asn Tyr Ser
1               5                   10                  15

Gly Asp Thr Ala Ser Gln Val Asp
            20

<210> SEQ ID NO 4
<211> LENGTH: 23
<212> TYPE: PRT
<213> ORGANISM: Artificial Sequence
<220> FEATURE:
<223> OTHER INFORMATION: A synthetic inclusion body fusion partner.

<400> SEQUENCE: 4

Gly Ser Gly Gln Gly Gln Ala Gln Tyr Leu Ala Ala Ser Leu Val Val
1               5                   10                  15

Phe Thr Asn Tyr Ser Gly Asp
            20

<210> SEQ ID NO 5
<211> LENGTH: 18
<212> TYPE: PRT
<213> ORGANISM: Artificial Sequence
<220> FEATURE:
<223> OTHER INFORMATION: A synthetic inclusion body fusion partner.

<400> SEQUENCE: 5

Gly Ser Gln Tyr Leu Ala Ala Ser Leu Val Val Phe Thr Asn Tyr Ser
1               5                   10                  15

Gly Asp

<210> SEQ ID NO 6
<211> LENGTH: 24
<212> TYPE: PRT
<213> ORGANISM: Artificial Sequence
<220> FEATURE:
<223> OTHER INFORMATION: A synthetic inclusion body fusion partner.

<400> SEQUENCE: 6

Gly Ser Gln Tyr Leu Ala Ala Val Leu Val Val Phe Thr Asn Tyr Ser
1               5                   10                  15

Gly Asp Thr Ala Ser Gln Val Asp
            20

<210> SEQ ID NO 7
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 7

Gly Ser Gly Gln Gly Gln Ala Gln Tyr Leu Thr Ala Ser Leu Val Lys
1               5                   10                  15

Phe Thr Asn Tyr Ser Gly Asp Thr Ala Ser Gln Val Asp
            20                  25

<210> SEQ ID NO 8
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 8

Gly Ser Gly Gln Gly Gln Ala Gln Tyr Leu Thr Ala Ser Leu Val Gln
1               5                   10                  15

Phe Thr Asn Tyr Ser Gly Asp Thr Ala Ser Gln Val Asp
            20                  25

<210> SEQ ID NO 9
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 9

Gly Ser Gly Gln Gly Gln Ala Gln Tyr Leu Pro Ala Ser Leu Val Lys
1               5                   10                  15

Phe Thr Asn Tyr Ser Gly Asp Thr Ala Ser Gln Val Asp
            20                  25

<210> SEQ ID NO 10
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 10

Gly Ser Gly Gln Gly Gln Ala Gln Tyr Leu Pro Ala Ser Leu Val Gln
1               5                   10                  15

-continued

Phe Thr Asn Tyr Ser Gly Asp Thr Ala Ser Gln Val Asp
            20                  25

<210> SEQ ID NO 11
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 11

Gly Ser Gly Gln Gly Gln Ala Gln Tyr Leu Ala Ala Ser Leu Val Lys
1               5                   10                  15

Phe Thr Asn Tyr Ser Gly Asp Thr Ala Ser Gln Val Asp
            20                  25

<210> SEQ ID NO 12
<211> LENGTH: 29
<212> TYPE: PRT
<213> ORGANISM: Artificial Sequence
<220> FEATURE:
<223> OTHER INFORMATION: An inclusion body fusion partner.

<400> SEQUENCE: 12

Gly Ser Gly Gln Gly Gln Ala Gln Tyr Leu Ala Ala Ser Leu Val Gln
1               5                   10                  15

Phe Thr Asn Tyr Ser Gly Asp Thr Ala Ser Gln Val Asp
            20                  25

<210> SEQ ID NO 13
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 13

Gly Ser Gly Gln Gly Gln Ala Gln Tyr Leu Ser Ala Ser Leu Val Lys
1               5                   10                  15

Phe Thr Asn Tyr Ser Gly Asp Thr Ala Ser Gln Val Asp
            20                  25

<210> SEQ ID NO 14
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 14

Gly Ser Gly Gln Gly Gln Ala Gln Tyr Leu Ser Ala Ser Leu Val Gln
1               5                   10                  15

Phe Thr Asn Tyr Ser Gly Asp Thr Ala Ser Gln Val Asp
            20                  25

<210> SEQ ID NO 15
<211> LENGTH: 29
<212> TYPE: PRT
<213> ORGANISM: Artificial Sequence
<220> FEATURE:
<223> OTHER INFORMATION: A synthetic inclusion body fusion partner.

<400> SEQUENCE: 15

Gly Ser Gly Gln Gly Gln Ala Gln Tyr Leu Ala Ala Val Leu Val Val
1               5                   10                  15

-continued

```
Phe Thr Asn Tyr Ser Gly Asp Thr Ala Ser Gln Val Asp
            20                  25

<210> SEQ ID NO 16
<211> LENGTH: 31
<212> TYPE: PRT
<213> ORGANISM: Artificial Sequence
<220> FEATURE:
<223> OTHER INFORMATION: A synthetic inclusion body fusion partner.

<400> SEQUENCE: 16

Ala Glu Glu Glu Glu Ile Leu Leu Glu Val Ser Leu Val Phe Lys Val
1               5                   10                  15

Lys Glu Phe Ala Pro Asp Ala Pro Leu Phe Thr Gly Pro Ala Tyr
            20                  25                  30

<210> SEQ ID NO 17
<211> LENGTH: 8
<212> TYPE: PRT
<213> ORGANISM: Artificial Sequence
<220> FEATURE:
<223> OTHER INFORMATION: A synthetic amino acid sequence of T7 tag.

<400> SEQUENCE: 17

Met Ala Ser Met Thr Gly Gly Gln
1               5

<210> SEQ ID NO 18
<211> LENGTH: 24
<212> TYPE: DNA
<213> ORGANISM: Artificial Sequence
<220> FEATURE:
<223> OTHER INFORMATION: A synthetic nucleotide sequence of T7 tag.

<400> SEQUENCE: 18
atggctagca tgactggtgg acag                                          24

<210> SEQ ID NO 19
<211> LENGTH: 25
<212> TYPE: PRT
<213> ORGANISM: Artificial Sequence
<220> FEATURE:
<223> OTHER INFORMATION: A synthetic amino acid sequence of GST-Tag.

<400> SEQUENCE: 19

Met Ser Pro Ile Leu Gly Tyr Trp Lys Ile Lys Gly Leu Val Gln Pro
1               5                   10                  15

Thr Arg Leu Leu Leu Glu Tyr Leu Glu
            20                  25

<210> SEQ ID NO 20
<211> LENGTH: 75
<212> TYPE: DNA
<213> ORGANISM: Artificial Sequence
<220> FEATURE:
<223> OTHER INFORMATION: A synthetic nucleotide sequence of GST-Tag.

<400> SEQUENCE: 20
atgtccccca tactaggtta ttggaaaata aagggccttg tgcaacccac tcgacttctt    60
ttggaatatc ttgaa                                                    75

<210> SEQ ID NO 21
<211> LENGTH: 23
<212> TYPE: PRT
<213> ORGANISM: Artificial Sequence
<220> FEATURE:
```

```
<223> OTHER INFORMATION: A synthetic amino acid sequence of
      Lactamase-Tag.

<400> SEQUENCE: 21

Met Ser Ile Gln His Phe Arg Val Ala Leu Ile Pro Phe Phe Ala Ala
 1               5                   10                  15

Phe Ser Leu Pro Val Phe Ala
            20

<210> SEQ ID NO 22
<211> LENGTH: 69
<212> TYPE: DNA
<213> ORGANISM: Artificial Sequence
<220> FEATURE:
<223> OTHER INFORMATION: A synthetic nucleotide sequence of
      Lactamase-Tag.

<400> SEQUENCE: 22
atgagtattc aacatttccg tgtcgccctt attcccttt ttgcggcatt ttcccttcct      60
gtttttgct                                                            69

<210> SEQ ID NO 23
<211> LENGTH: 85
<212> TYPE: PRT
<213> ORGANISM: Artificial Sequence
<220> FEATURE:
<223> OTHER INFORMATION: A synthetic amino acid sequence of
      alpha-factor.

<400> SEQUENCE: 23

Met Arg Phe Pro Ser Ile Phe Thr Ala Val Leu Phe Ala Ala Ser Ser
 1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
                85

<210> SEQ ID NO 24
<211> LENGTH: 255
<212> TYPE: DNA
<213> ORGANISM: Artificial Sequence
<220> FEATURE:
<223> OTHER INFORMATION: A synthetic nucleotide sequence of
      alpha-factor.

<400> SEQUENCE: 24
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta      240 tctctcgaga aaaga                                                     255

<210> SEQ ID NO 25
<211> LENGTH: 12
<212> TYPE: PRT
```

```
<213> ORGANISM: Artificial Sequence
<220> FEATURE:
<223> OTHER INFORMATION: A synthetic amino acid sequence of T7 Gene 10
      N-Term.

<400> SEQUENCE: 25

Met Ala Ser Met Thr Gly Gly Gln Gln Met Gly Arg
 1               5                  10

<210> SEQ ID NO 26
<211> LENGTH: 1581
<212> TYPE: DNA
<213> ORGANISM: Clostridium histolyticum

<400> SEQUENCE: 26
atgttaagaa gaaaagtatc aacactatta atgacagctt tgataactac ttcattttta      60
aattccaaac ccgtatatgc aaatccagta actaaatcca aggataataa cttaaaagaa     120
gtacaacaag ttacaagcaa gagtaataaa acaaaaatc aaaaagtaac tattatgtac      180
tattgcgacg cagataataa cttggaagga agtctattaa atgatatcga ggaaatgaaa     240
acaggatata aggatagtcc taatttaaat ttaattgctc ttgtagacag atccccaaga     300
tatagcagtg acgaaaaagt tttaggtgaa gattttagtg atacacgtct ttataagatt     360
gaacacaata aggcaaatag attagacggt aaaaatgaat ttccagaaat aagtactact     420
agtaaatatg aagctaacat gggggatcct gaagttctta aaaaatttat tgattattgt     480
aaatctaatt atgaggctga taaatatgtg cttataatgg ctaatcatgg tggtggtgca     540
agggaaaaat caaatccaag attaaataga gcaatttgct gggatgatag taaccttgat     600
aaaaatggtg aagcagactg cctttatatg ggtgaaattt cagatcattt aacagaaaaa     660
caatcagttg atttacttgc ctttgatgcg tgccttatgg gaactgcaga agtagcgtat     720
cagtatagac caggtaatgg aggattttct gccgatactt tagttgcttc aagcccagta     780
gtttggggtc ctggattcaa atatgataag attttcgata ggataaaagc tggtggagga     840
actaataatg aggatgattt aactttaggt ggtaaagaac aaaactttga tcctgcaacc     900
attaccaatg agcaattagg tgcattattt gtagaagagc aaagagactc aacacatgcc     960
aatggtcgct atgatcaaca cttaagcttt tatgatttaa agaaagctga atcagtaaaa    1020
agagccatag ataatttagc tgttaatcta agtaatgaaa caaaaaatc tgaaattgaa     1080 aaattaagag gaagtggaat tcatacagat ttaatgcatt acttcgatga atattctgaa    1140
ggagaatggg ttgaatatcc ttattttgac gtgtatgatt tatgtgaaaa ataaataaa     1200 agtgaaaatt ttagtagtaa aactaaagat ttagcttcaa atgctatgaa taaattaaat    1260
gaaatgatag tttattcttt tggagaccct agtaataatt ttaaagaagg aaaaaatgga    1320
ttgagtatat tcttacctaa tggagataaa aaatattcaa cttattatac atcaaccaag    1380 ataccctcatt ggactatgca agttggtat aattcaatag atacagttaa atatggattg    1440
aatccttacg gaaaattaag ttggtgtaaa gatggacaag atcctgaaat aaataaagtt   1500
ggaaattggt ttgaacttct agattcttgg tttgataaaa ctaatgatgt aactggagga    1560
gttaatcatt accaatggta a                                              1581

<210> SEQ ID NO 27
<211> LENGTH: 1431
<212> TYPE: DNA
<213> ORGANISM: Clostridium histolyticum

<400> SEQUENCE: 27
```

```
aacaaaaatc aaaaagtaac tattatgtac tattgcgacg cagataataa cttggaagga    60
agtctattaa atgatatcga ggaaatgaaa acaggatata aggatagtcc taatttaaat   120
ttaattgctc ttgtagacag atccccaaga tatagcagtg acgaaaaagt tttaggtgaa   180
gattttagtg atacacgtct ttataagatt gaacacaata aggcaaatag attagacggt   240
aaaaatgaat ttccagaaat aagtactact agtaaatatg aagctaacat ggggatcct    300
gaagttctta aaaatttat tgattattgt aaatctaatt atgaggctga taaatatgtg    360
cttataatgg ctaatcatgg tggtggtgca agggaaaaat caaatccaag attaaataga   420
gcaatttgct gggatgatag taaccttgat aaaaatggtg aagcagactg cctttatatg   480
ggtgaaattt cagatcattt aacagaaaaa caatcagttg atttacttgc ctttgatgcg   540
tgccttatgg gaactgcaga agtagcgtat cagtatagac caggtaatgg aggattttct   600
gccgatactt tagttgcttc aagcccagta gtttggggtc ctggattcaa atatgataag   660
attttcgata ggataaaagc tggtggagga actaataatg aggatgattt aactttaggt   720
ggtaaagaac aaaactttga tcctgcaacc attaccaatg agcaattagg tgcattattt   780
gtagaagagc aaagagactc aacacatgcc aatggtcgct atgatcaaca cttaagcttt   840
tatgatttaa agaaagctga atcagtaaaa agagccatag ataatttagc tgttaatcta   900
agtaatgaaa acaaaaaatc tgaaattgaa aattaagag gaagtggaat tcatacagat   960
ttaatgcatt acttcgatga atattctgaa ggagaatggg ttgaatatcc ttattttgac  1020
gtgtatgatt tatgtgaaaa aataaataaa agtgaaaatt ttagtagtaa aactaaagat  1080
ttagcttcaa atgctatgaa taaattaaat gaaatgatag tttattcttt tggagaccct  1140
agtaataatt ttaaagaagg aaaaaatgga ttgagtatat tcttacctaa tggagataaa  1200
aaatattcaa cttattatac atcaaccaag atacctcatt ggactatgca agttggtat   1260
aattcaatag atacagttaa atatggattg aatccttacg gaaaattaag ttggtgtaaa  1320
gatggacaag atcctgaaat aaataaagtt ggaaattggt ttgaacttct agattcttgg  1380
tttgataaaa ctaatgatgt aactggagga gttaatcatt accaatggta a           1431
```

<210> SEQ ID NO 28
<211> LENGTH: 526
<212> TYPE: PRT
<213> ORGANISM: Clostridium histolyticum

<400> SEQUENCE: 28

```
Met Leu Arg Arg Lys Val Ser Thr Leu Met Thr Ala Leu Ile Thr
  1               5                  10                  15

Thr Ser Phe Leu Asn Ser Lys Pro Val Tyr Ala Asn Pro Val Thr Lys
                 20                  25                  30

Ser Lys Asp Asn Asn Leu Lys Glu Val Gln Gln Val Thr Ser Lys Ser
             35                  40                  45

Asn Lys Asn Lys Asn Gln Lys Val Thr Ile Met Tyr Tyr Cys Asp Ala
         50                  55                  60

Asp Asn Asn Leu Glu Gly Ser Leu Leu Asn Asp Ile Glu Glu Met Lys
 65                  70                  75                  80

Thr Gly Tyr Lys Asp Ser Pro Asn Leu Asn Leu Ile Ala Leu Val Asp
                 85                  90                  95

Arg Ser Pro Arg Tyr Ser Ser Asp Glu Lys Val Leu Gly Glu Asp Phe
            100                 105                 110

Ser Asp Thr Arg Leu Tyr Lys Ile Glu His Asn Lys Ala Asn Arg Leu
        115                 120                 125
```

Asp Gly Lys Asn Glu Phe Pro Glu Ile Ser Thr Thr Ser Lys Tyr Glu
    130                 135                 140

Ala Asn Met Gly Asp Pro Glu Val Leu Lys Lys Phe Ile Asp Tyr Cys
145                 150                 155                 160

Lys Ser Asn Tyr Glu Ala Asp Lys Tyr Val Leu Ile Met Ala Asn His
                165                 170                 175

Gly Gly Gly Ala Arg Glu Lys Ser Asn Pro Arg Leu Asn Arg Ala Ile
            180                 185                 190

Cys Trp Asp Asp Ser Asn Leu Asp Lys Asn Gly Glu Ala Asp Cys Leu
        195                 200                 205

Tyr Met Gly Glu Ile Ser Asp His Leu Thr Glu Lys Gln Ser Val Asp
    210                 215                 220

Leu Leu Ala Phe Asp Ala Cys Leu Met Gly Thr Ala Glu Val Ala Tyr
225                 230                 235                 240

Gln Tyr Arg Pro Gly Asn Gly Phe Ser Ala Asp Thr Leu Val Ala
                245                 250                 255

Ser Ser Pro Val Val Trp Gly Pro Phe Lys Tyr Asp Lys Ile Phe
            260                 265                 270

Asp Arg Ile Lys Ala Gly Gly Gly Thr Asn Asn Glu Asp Asp Leu Thr
        275                 280                 285

Leu Gly Gly Lys Glu Gln Asn Phe Asp Pro Ala Thr Ile Thr Asn Glu
    290                 295                 300

Gln Leu Gly Ala Leu Phe Val Glu Glu Gln Arg Asp Ser Thr His Ala
305                 310                 315                 320

Asn Gly Arg Tyr Asp Gln His Leu Ser Phe Tyr Asp Leu Lys Lys Ala
                325                 330                 335

Glu Ser Val Lys Arg Ala Ile Asp Asn Leu Ala Val Asn Leu Ser Asn
            340                 345                 350

Glu Asn Lys Lys Ser Glu Ile Glu Lys Leu Arg Gly Ser Gly Ile His
        355                 360                 365

Thr Asp Leu Met His Tyr Phe Asp Glu Tyr Ser Glu Gly Glu Trp Val
    370                 375                 380

Glu Tyr Pro Tyr Phe Asp Val Tyr Asp Leu Cys Glu Lys Ile Asn Lys
385                 390                 395                 400

Ser Glu Asn Phe Ser Ser Lys Thr Lys Asp Leu Ala Ser Asn Ala Met
                405                 410                 415

Asn Lys Leu Asn Glu Met Ile Val Tyr Ser Phe Gly Asp Pro Ser Asn
            420                 425                 430

Asn Phe Lys Glu Gly Lys Asn Gly Leu Ser Ile Phe Leu Pro Asn Gly
        435                 440                 445

Asp Lys Lys Tyr Ser Thr Tyr Tyr Thr Ser Thr Lys Ile Pro His Trp
    450                 455                 460

Thr Met Gln Ser Trp Tyr Asn Ser Ile Asp Thr Val Lys Tyr Gly Leu
465                 470                 475                 480

Asn Pro Tyr Gly Lys Leu Ser Trp Cys Lys Asp Gly Gln Asp Pro Glu
                485                 490                 495

Ile Asn Lys Val Gly Asn Trp Phe Glu Leu Leu Asp Ser Trp Phe Asp
            500                 505                 510

Lys Thr Asn Asp Val Thr Gly Gly Val Asn His Tyr Gln Trp
        515                 520                 525

<210> SEQ ID NO 29
<211> LENGTH: 476
<212> TYPE: PRT
<213> ORGANISM: Clostridium histolyticum

<400> SEQUENCE: 29

```
Asn Lys Asn Gln Lys Val Thr Ile Met Tyr Tyr Cys Asp Ala Asp Asn
 1               5                   10                  15
Asn Leu Glu Gly Ser Leu Leu Asn Asp Ile Glu Glu Met Lys Thr Gly
            20                  25                  30
Tyr Lys Asp Ser Pro Asn Leu Asn Leu Ile Ala Leu Val Asp Arg Ser
        35                  40                  45
Pro Arg Tyr Ser Ser Asp Glu Lys Val Leu Gly Glu Asp Phe Ser Asp
50                  55                  60
Thr Arg Leu Tyr Lys Ile Glu His Asn Lys Ala Asn Arg Leu Asp Gly
65                  70                  75                  80
Lys Asn Glu Phe Pro Glu Ile Ser Thr Thr Ser Lys Tyr Glu Ala Asn
                85                  90                  95
Met Gly Asp Pro Glu Val Leu Lys Lys Phe Ile Asp Tyr Cys Lys Ser
            100                 105                 110
Asn Tyr Glu Ala Asp Lys Tyr Val Leu Ile Met Ala Asn His Gly Gly
        115                 120                 125
Gly Ala Arg Glu Lys Ser Asn Pro Arg Leu Asn Arg Ala Ile Cys Trp
130                 135                 140
Asp Asp Ser Asn Leu Asp Lys Asn Gly Glu Ala Asp Cys Leu Tyr Met
145                 150                 155                 160
Gly Glu Ile Ser Asp His Leu Thr Glu Lys Gln Ser Val Asp Leu Leu
                165                 170                 175
Ala Phe Asp Ala Cys Leu Met Gly Thr Ala Glu Val Ala Tyr Gln Tyr
            180                 185                 190
Arg Pro Gly Asn Gly Gly Phe Ser Ala Asp Thr Leu Val Ala Ser Ser
        195                 200                 205
Pro Val Val Trp Gly Pro Gly Phe Lys Tyr Asp Lys Ile Phe Asp Arg
210                 215                 220
Ile Lys Ala Gly Gly Gly Thr Asn Asn Glu Asp Asp Leu Thr Leu Gly
225                 230                 235                 240
Gly Lys Glu Gln Asn Phe Asp Pro Ala Thr Ile Thr Asn Glu Gln Leu
                245                 250                 255
Gly Ala Leu Phe Val Glu Glu Gln Arg Asp Ser Thr His Ala Asn Gly
            260                 265                 270
Arg Tyr Asp Gln His Leu Ser Phe Tyr Asp Leu Lys Lys Ala Glu Ser
        275                 280                 285
Val Lys Arg Ala Ile Asp Asn Leu Ala Val Asn Leu Ser Asn Glu Asn
290                 295                 300
Lys Lys Ser Glu Ile Glu Lys Leu Arg Gly Ser Gly Ile His Thr Asp
305                 310                 315                 320
Leu Met His Tyr Phe Asp Glu Tyr Ser Glu Gly Glu Trp Val Glu Tyr
                325                 330                 335
Pro Tyr Phe Asp Val Tyr Asp Leu Cys Glu Lys Ile Asn Lys Ser Glu
            340                 345                 350
Asn Phe Ser Ser Lys Thr Lys Asp Leu Ala Ser Asn Ala Met Asn Lys
        355                 360                 365
Leu Asn Glu Met Ile Val Tyr Ser Phe Gly Asp Pro Ser Asn Asn Phe
370                 375                 380
Lys Glu Gly Lys Asn Gly Leu Ser Ile Phe Leu Pro Asn Gly Asp Lys
385                 390                 395                 400
Lys Tyr Ser Thr Tyr Tyr Thr Ser Thr Lys Ile Pro His Trp Thr Met
                405                 410                 415
```

```
Gln Ser Trp Tyr Asn Ser Ile Asp Thr Val Lys Tyr Gly Leu Asn Pro
            420                 425                 430
Tyr Gly Lys Leu Ser Trp Cys Lys Asp Gly Gln Asp Pro Glu Ile Asn
        435                 440                 445
Lys Val Gly Asn Trp Phe Glu Leu Leu Asp Ser Trp Phe Asp Lys Thr
    450                 455                 460
Asn Asp Val Thr Gly Gly Val Asn His Tyr Gln Trp
465                 470                 475

<210> SEQ ID NO 30
<211> LENGTH: 34
<212> TYPE: DNA
<213> ORGANISM: Artificial Sequence
<220> FEATURE:
<223> OTHER INFORMATION: A synthetic primer.

<400> SEQUENCE: 30
tgcatttcta gaattgtgaa ttgttatccg ctca                            34

<210> SEQ ID NO 31
<211> LENGTH: 24
<212> TYPE: DNA
<213> ORGANISM: Artificial Sequence
<220> FEATURE:
<223> OTHER INFORMATION: A synthetic primer.

<400> SEQUENCE: 31
tcaaagatct tatcgactgc acgg                                       24

<210> SEQ ID NO 32
<211> LENGTH: 261
<212> TYPE: DNA
<213> ORGANISM: Artificial Sequence
<220> FEATURE:
<223> OTHER INFORMATION: A synthetic PCR amplication product.

<400> SEQUENCE: 32
tcaaagatct tatcgactgc acggtgcacc aatgcttctg gcgtcaggca gccatcggaa    60
gctgtggtat ggctgtgcag gtcgtaaatc actgcataat tcgtgtcgct caaggcgcac   120
tcccgttctg gataatgttt tttgcgccga catcataacg gttctggcaa atattctgaa   180
atgagctgtt gacaattaat catcggctcg tataatgtgt ggaattgtga gcggataaca   240
attcacaatt ctagaaatgc a                                            261

<210> SEQ ID NO 33
<211> LENGTH: 33
<212> TYPE: DNA
<213> ORGANISM: Artificial Sequence
<220> FEATURE:
<223> OTHER INFORMATION: A synthetic primer.

<400> SEQUENCE: 33
cctgacgtcc cggatgaatg tcagctactg ggc                             33

<210> SEQ ID NO 34
<211> LENGTH: 33
<212> TYPE: DNA
<213> ORGANISM: Artificial Sequence
<220> FEATURE:
<223> OTHER INFORMATION: A synthetic primer.

<400> SEQUENCE: 34
ggctgcgcaa aggagaaaat accgcatcag gaa                             33
```

<210> SEQ ID NO 35
<211> LENGTH: 42
<212> TYPE: DNA
<213> ORGANISM: Artificial Sequence
<220> FEATURE:
<223> OTHER INFORMATION: A synthetic primer.

<400> SEQUENCE: 35
agagctcata tgttaagaag aaaagtatca acactattaa tg                          42

<210> SEQ ID NO 36
<211> LENGTH: 39
<212> TYPE: DNA
<213> ORGANISM: Artificial Sequence
<220> FEATURE:
<223> OTHER INFORMATION: A synthetic primer.

<400> SEQUENCE: 36
ttgctcgagt taccattggt aatgattaac tcctccagt                              39

<210> SEQ ID NO 37
<211> LENGTH: 40
<212> TYPE: DNA
<213> ORGANISM: Artificial Sequence
<220> FEATURE:
<223> OTHER INFORMATION: A synthetic primer.

<400> SEQUENCE: 37
tatacatatg aatccagtaa ctaaatccaa ggataataac                             40

<210> SEQ ID NO 38
<211> LENGTH: 33
<212> TYPE: DNA
<213> ORGANISM: Artificial Sequence
<220> FEATURE:
<223> OTHER INFORMATION: A synthetic primer.

<400> SEQUENCE: 38
cctaggatcc cccatgttag cttcatattt act                                    33

<210> SEQ ID NO 39
<211> LENGTH: 37
<212> TYPE: DNA
<213> ORGANISM: Artificial Sequence
<220> FEATURE:
<223> OTHER INFORMATION: A synthetic primer.

<400> SEQUENCE: 39
tatacatatg aacaaaaatc aaaagtaac tattatg                                 37

<210> SEQ ID NO 40
<211> LENGTH: 57
<212> TYPE: DNA
<213> ORGANISM: Artificial Sequence
<220> FEATURE:
<223> OTHER INFORMATION: A synthetic primer.

<400> SEQUENCE: 40
atacatatgg ctagcatgac tggtggacag aacaaaaatc aaaagtaac tattatg           57

<210> SEQ ID NO 41
<211> LENGTH: 36
<212> TYPE: DNA
<213> ORGANISM: Artificial Sequence
<220> FEATURE:
<223> OTHER INFORMATION: A synthetic primer.

<400> SEQUENCE: 41
ttcctgagct ccaccaccat gattagccat tataag						36

<210> SEQ ID NO 42
<211> LENGTH: 42
<212> TYPE: DNA
<213> ORGANISM: Artificial Sequence
<220> FEATURE:
<223> OTHER INFORMATION: A synthetic primer.

<400> SEQUENCE: 42
ggtggagctc aggaaaaatc aaatccacag ttaaatcagg ca					42

<210> SEQ ID NO 43
<211> LENGTH: 33
<212> TYPE: DNA
<213> ORGANISM: Artificial Sequence
<220> FEATURE:
<223> OTHER INFORMATION: A synthetic primer.

<400> SEQUENCE: 43
ggtggagctc aggcaatttg ctgggatgat agt						33

<210> SEQ ID NO 44
<211> LENGTH: 1587
<212> TYPE: DNA
<213> ORGANISM: Clostridium histolyticum

<400> SEQUENCE: 44

| | |
|---|---|
| atgttaagaa gaaaagtatc aacactatta atgacagctt tgataactac ttcattttta | 60 |
| aattccaaac ccgtatatgc aaatccagta actaaatcca aggataataa cttaaaagaa | 120 |
| gtacaacaag ttacaagcaa gagtaataaa acaaaaatc aaaagtaac tattatgtac | 180 |
| tattgcgacg cagataataa cttggaagga agtctattaa atgatatcga ggaaatgaaa | 240 |
| acaggatata aggatagtcc taatttaaat ttaattgctc ttgtagacag atccccaaga | 300 |
| tatagcagtg acgaaaaagt tttaggtgaa gattttagtg atacacgtct ttataagatt | 360 |
| gaacacaata aggcaaatag attagacggt aaaaatgaat tccagaaaat aagtactact | 420 |
| agtaaatatg aagctaacat gggggatcct gaagttctta aaaaatttat tgattattgt | 480 |
| aaatctaatt atgaggctga taaatatgtg cttataatgg ctaatcatgg tggtggtgca | 540 |
| agggaaaaat caaatccaag attaaataga gcaatttgct gggatgatag taaccttgat | 600 |
| aaaaatggtg aagcagactg ccttttatatg ggtgaaattt cagatcattt aacagaaaaa | 660 |
| caatcagttg atttacttgc ctttgatgcg tgccttatgg gaactgcaga agtagcgtat | 720 |
| cagtatagac caggtaatgg aggattttct gccgatactt tagttgcttc aagcccagta | 780 |
| gtttggggtc ctggattcaa atatgataag attttcgata ggataaaagc tggtggagga | 840 |
| actaataatg aggatgattt aactttaggt ggtaaagaac aaaactttga tcctgcaacc | 900 |
| attaccaatg agcaattagg tgcattattt gtagaagagc aaagagactc aacacatgcc | 960 |
| aatggtcgct atgatcaaca cttaagcttt tatgatttaa agaagctgaa tcagtaaaaa | 1020 |
| agagccatag ataatttagc tgttaatcta gtaatgaaa acaaaaaatc tgaaattgaa | 1080 |
| aaattaagag gaagtggaat tcatacagat ttaatgcatt acttcgatga atattctgaa | 1140 |
| ggagaatggg ttgaatatcc ttatttgac gtgtatgatt tatgtgaaaa aataaataaa | 1200 |
| agtgaaaatt ttagtagtaa aactaaagat ttagcttcaa atgctatgaa taaattaaat | 1260 |
| gaaatgatag tttattcttt tggagaccct agtaataatt ttaaagaagg aaaaaatgga | 1320 |

```
ttgagtatat tcttacctaa tggagataaa aaatattcaa cttattatac atcaaccaag    1380
atacctcatt ggactatgca aagttggtat aattcaatag atacagttaa atatggattg    1440
aatccttacg gaaaattaag ttggtgtaaa gatggacaag atcctgaaat aaataaagtt    1500
ggaaattggt ttgaacttct agattcttgg tttgataaaa ctaatgatgt aactggagga    1560
gttaatcatt accaatggta actcgag                                        1587
```

<210> SEQ ID NO 45
<211> LENGTH: 156
<212> TYPE: PRT
<213> ORGANISM: Artificial Sequence
<220> FEATURE:
<223> OTHER INFORMATION: A synthetic N-terminal sequence of the cloned
      T7 tag-clostripain.

<400> SEQUENCE: 45

```
Met Ala Ser Met Thr Gly Gly Gln Asn Lys Asn Gln Lys Val Thr Ile
  1               5                  10                  15

Met Tyr Tyr Cys Asp Ala Asp Asn Asn Leu Glu Gly Ser Leu Leu Asn
             20                  25                  30

Asp Ile Glu Glu Met Lys Thr Gly Tyr Lys Asp Ser Pro Asn Leu Asn
         35                  40                  45

Leu Ile Ala Leu Val Asp Arg Ser Pro Arg Tyr Ser Ser Asp Glu Lys
     50                  55                  60

Val Leu Gly Glu Asp Phe Ser Asp Thr Arg Leu Tyr Lys Ile Glu His
 65                  70                  75                  80

Asn Lys Ala Asn Arg Leu Asp Gly Lys Asn Glu Phe Pro Glu Ile Ser
                 85                  90                  95

Thr Thr Ser Lys Tyr Glu Ala Asn Met Gly Asp Pro Glu Val Leu Lys
            100                 105                 110

Lys Phe Ile Asp Tyr Cys Lys Ser Asn Tyr Glu Ala Asp Lys Tyr Val
        115                 120                 125

Leu Ile Met Ala Asn His Gly Gly Gly Ala Arg Glu Lys Ser Asn Pro
    130                 135                 140

Arg Leu Asn Arg Ala Ile Cys Trp Asp Asp Ser Asn
145                 150                 155
```

<210> SEQ ID NO 46
<211> LENGTH: 468
<212> TYPE: DNA
<213> ORGANISM: Artificial Sequence
<220> FEATURE:
<223> OTHER INFORMATION: A synthetic N-terminal sequence of the cloned
      T7 tag-clostripain.

<400> SEQUENCE: 46

```
atggctagca tgactggtgg acagaacaaa atcaaaaag taactattat gtactattgc      60
gacgcagata taacttgga aggaagtcta ttaaatgata tcgaggaaat gaaaacagga    120
tataaggata gtcctaattt aaatttaatt gctcttgtag acagatcccc aagatatagc    180
agtgacgaaa aagttttagg tgaagatttt agtgatacac gtctttataa gattgaacac    240
aataaggcaa atagattaga cggtaaaaat gaatttccag aaataagtac tactagtaaa    300
tatgaagcta acatggggga tcctgaagtt cttaaaaaat ttattgatta ttgtaaatct    360
aattatgagg ctgataaata tgtgcttata atggctaatc atggtggtgg tgcaagggaa    420
aaatcaaatc caagattaaa tagagcaatt tgctgggatg atagtaac                 468
```

```
<210> SEQ ID NO 47
<211> LENGTH: 234
<212> TYPE: PRT
<213> ORGANISM: Artificial Sequence
<220> FEATURE:
<223> OTHER INFORMATION: A synthetic amino acid sequence of a mutated
      clostripain.

<400> SEQUENCE: 47

Ala Asn Met Gly Asp Pro Glu Val Leu Lys Lys Phe Ile Asp Tyr Cys
  1               5                  10                  15

Lys Ser Asn Tyr Glu Ala Asp Lys Tyr Val Leu Ile Met Ala Asn His
             20                  25                  30

Gly Gly Gly Ala Gln Glu Lys Ser Asn Pro Gln Leu Asn Gln Ala Ile
         35                  40                  45

Cys Trp Asp Asp Ser Asn Leu Asp Lys Asn Gly Glu Ala Asp Cys Leu
     50                  55                  60

Tyr Met Gly Glu Ile Ser Asp His Leu Thr Glu Lys Gln Ser Val Asp
 65                  70                  75                  80

Leu Leu Ala Phe Asp Ala Cys Leu Met Gly Thr Ala Glu Val Ala Tyr
                 85                  90                  95

Gln Tyr Arg Pro Gly Asn Gly Phe Ser Ala Asp Thr Leu Val Ala
            100                 105                 110

Ser Ser Pro Val Val Trp Gly Pro Gly Phe Lys Tyr Asp Lys Ile Phe
        115                 120                 125

Asp Arg Ile Lys Ala Gly Gly Thr Asn Asn Glu Asp Asp Leu Thr
130                 135                 140

Leu Gly Gly Lys Glu Gln Asn Phe Asp Pro Ala Thr Ile Thr Asn Glu
145                 150                 155                 160

Gln Leu Gly Ala Leu Phe Val Glu Glu Gln Arg Asp Ser Thr His Ala
                165                 170                 175

Asn Gly Arg Tyr Asp Gln His Leu Ser Phe Tyr Asp Leu Lys Lys Ala
            180                 185                 190

Glu Ser Val Lys Arg Ala Ile Asp Asn Leu Ala Val Asn Leu Ser Asn
        195                 200                 205

Glu Asn Lys Lys Ser Glu Ile Glu Lys Leu Arg Gly Ser Gly Ile His
    210                 215                 220

Thr Asp Leu Met His Tyr Phe Asp Glu Tyr
225                 230

<210> SEQ ID NO 48
<211> LENGTH: 702
<212> TYPE: DNA
<213> ORGANISM: Artificial Sequence
<220> FEATURE:
<223> OTHER INFORMATION: A synthetic nucleotide sequence of a mutated
      clostripain.

<400> SEQUENCE: 48
gctaacatgg gggatcctga agttcttaaa aaatttattg attattgtaa atctaattat      60
gaggctgata atatgtgct tataatggct aatcatggtg gtggagctca ggaaaaatca     120
aatccacagt taaatcaggc aatttgctgg gatgatagta accttgataa aaatggtgaa     180
gcagactgcc tttatatggg tgaaatttca gatcatttaa cagaaaaaca atcagttgat     240
ttacttgcct ttgatgcgtg ccttatggga actgcagaag tagcgtatca gtatagacca     300
ggtaatggag gatttttctgc cgatactttta gttgcttcaa gcccagtagt ttggggtcct     360
ggattcaaat atgataagat tttcgatagg ataaaagctg gtggaggaac taataatgag     420
```

```
gatgatttaa ctttaggtgg taaagaacaa aactttgatc ctgcaaccat taccaatgag    480
caattaggtg cattatttgt agaagagcaa agagactcaa cacatgccaa tggtcgctat    540
gatcaacact taagctttta tgatttaaag aaagctgaat cagtaaaaag agccatagat    600
aatttagctg ttaatctaag taatgaaaac aaaaaatctg aaattgaaaa attaagagga    660
agtggaattc atacagattt aatgcattac ttcgatgaat at                       702
```